US008691215B2

(12) United States Patent
Dimmock et al.

(10) Patent No.: US 8,691,215 B2
(45) Date of Patent: Apr. 8, 2014

(54) ANTI-VIRAL PROTECTION WITH VIRUSES CONTAINING DEFECTIVE GENOME SEGMENTS

(75) Inventors: Nigel Dimmock, Leamington Spa (GB); Andrew Easton, Warwick (GB)

(73) Assignee: The University of Warwick, Coventry (GB)

( * ) Notice: Subject to any disclaimer, the term of this patent is extended or adjusted under 35 U.S.C. 154(b) by 258 days.

(21) Appl. No.: 13/132,593

(22) PCT Filed: Dec. 8, 2009

(86) PCT No.: PCT/GB2009/051666

§ 371 (c)(1), (2), (4) Date: Jun. 2, 2011

(87) PCT Pub. No.: WO2010/067109

PCT Pub. Date: Jun. 17, 2010

(65) Prior Publication Data

US 2011/0243896 A1 Oct. 6, 2011

(30) Foreign Application Priority Data

Dec. 12, 2008 (GB) .................................. 0822672.2

(51) Int. Cl.
*A01N 63/00* (2006.01)
*C12N 7/00* (2006.01)

(52) U.S. Cl.
USPC ...................................... 424/93.6; 435/235.1

(58) Field of Classification Search
None
See application file for complete search history.

(56) References Cited

U.S. PATENT DOCUMENTS

2006/0057116 A1 3/2006 Kawaoka et al.
2009/0191158 A1 7/2009 Dimmock

FOREIGN PATENT DOCUMENTS

GB 2 437 799 B 8/2008
WO WO2006/051069 A 5/2006
WO WO 2007/135420 * 11/2007
WO WO 2007/135420 A2 11/2007

OTHER PUBLICATIONS

Strube et al., Molec. Biol. Rep., 1985, 10:237-243.*

Duhaut and Dimmock, "Heterologous Protection of Mice from a Lethal Human H1N1 Influenza A Virus Infection by H3N8 Equine Defective Interfering Virus: Comparison of Defective RNA Sequences Isolated from the DI Inoculum and Mouse Lung," *Virology* 248:241-253, 1998.

Marriott and Dimmock, "Defective Interfering Viruses and Their Potential as Antiviral Agents," *Rev. Med. Virol.* 20:51-62, 2010.

Pattnaik et al., "Infectious Defective Interfering Particles of VSV from Transcripts of a cNDA Clone," *Cell* 69:1011-1120, 1992.

Owen T. Gorman, et al.; "Evolution of Influenza A Virus PB2 Genes: Implications for Evolution of the Ribonucleoprotein Complex and Origin of Human Influenza A Virus"; Oct. 2009; Journal of Virology, vol. 64, No. 10; pp. 4893-4902.

S. Noble, et al.; "Characterization of Putative Defective Interfering (DI) A/WSN RNAs Isolated from the Lungs of Mice Protected from an Otherwise Lethal Respiratory Infection with Influenza Virus A/WSN (H1N1): A Subset of the Inoculum DI RNAs"; Department of Biological Sciences, University of Warwick, UK; Virology 210, pp. 9-19; (1995).

P. Jennings, et al.; "Does the Higher Order Structure of the Influenza Virus Ribonucleoprotein Guide Sequence Rearrangements in Influenza Viral RNA?"; Laboratory of Molecular Biology Medical Research Council Centre, England; vol. 34, pp. 619-627; Sep. 1983.

Mitnaul, Lyndon J. et al., "Balanced hemagglutinin and neuraminidase activities are critical for efficient replication of influenza A virus," Journal of Virology, v. 74, n. 13, Jul. 2000, p. 6016.

Mann et al, "Interfering vaccine (defective interfering inftuenza A virus) protects ferrets from influenza, and allows them to develop solid immunity to reinfection," Vaccine, Butterworth Scientific. Guildford, GB, v. 24, n. 20, May 15, 2006, p. 4291.

Dimmock, Nigel J. et al., "In vivo antiviral activity: defective interfering virus protects better against virulent Influenza A virus than avirulent virus," Journal of General Virology, v. 87, n. Part 5, May 1, 2006, pp. 1259-1265.

Almeida et al. "Nasal Delivery of Vaccines", Journal of Drug Targeting 1996, vol. 3, p. 455-467.

Duhaut, S.D. et al., "Defective influenza A virus generated entirely from plasmids: Its RNA is expressed in infected mouse lung and modulates disease," Journal of Virology Methods, v. 108, n. 1, Mar. 2003, pp. 75-82.

Duhaut, S.D. et al., "Defective segment 1 RNAs that interfere with production of infectious inftuenza A virus require at least 150 nucleotides of 5' sequence: Evidence from a plasmid-driven system," Journal of General Virology, v. 83, n. 2, Feb. 2002, pp. 403-411.

Duhaut, S.D. et al., "Approximately 150 Nucleotides from the 5' End of an Influenza A Segment 1 Defective Viron RNA are Needed for Genome Stability during Passage of Defective Virus in Infected Cells," Virology, v. 275, n. 2, Sep. 30, 2000, pp. 278-285.

International Search Report for International Application No. PCT/GB2007/001889, 8 pgs, Aug. 2008.

Lamb et al. "Orthomyxoviridae: The Viruses and Their Replication", Fields Virology, Third Edition, p. 1353-1395, (1996).

(Continued)

*Primary Examiner* — Nicole Kinsey White
(74) *Attorney, Agent, or Firm* — King & Schickli, PLLC

(57) ABSTRACT

The invention relates to virology and the prevention and/or treatment of viral infection and disease in animals, including birds and humans. The invention relates to the field of antiviral treatments. The invention further relates to methods of stimulating innate immunity and natural interferon production in humans or animals and in component parts of humans or animals, including cells and tissues. The invention also relates to the field of defective interfering (DI) viruses, including cloned DI viruses.

6 Claims, 7 Drawing Sheets

(56) References Cited

OTHER PUBLICATIONS

Von Magnus, "Propagation of the PR8 Strain of Inftuenza A Virus in Chick Embryos. III. Properties of the Incomplete Virus Produced in Serial Passages of Undiluted Virus", Acta Pathol. Microbiol. Scand. 1951, vol. 29, p. 157-181.
Nayak et al. "Defective-Interfering (D1) RNAs of Influenza Viruses: Origin, Structure, Expression, and Interference", Current Topics in Microbiology and Immunology 1985, vol. 114, p. 103-151.
Noble et al. "Defective Interfering Type A Equine Inftuenza Virus (H3N8) Protects Mice from Morbidity and Mortality Caused by Homologous and Heterologous Subtypes of Inftuenza A Virus", Journal of General Virology 1994, vol. 75, p. 3485-3491.
Noble et al. "Interfering Vaccine: A Novel Antiviral that Converts a Potentially Virulent Infection into one that is Subclinical and Immunizing", Vaccine 2004, vol. 22, p. 3018-3025.
Meier-Ewert et al. "The Role of the Neuraminidase of the Infecting Virus in the Production of Noninfectious (Von Magnus) Influenza Virus", Virology 1970, vol. 42, p. 794-798.
Fazekas et al. "The Production of Incomplete Virus Particles Among Inftuenza Strains Experiments in Eggs", Brit J. Exp. Path. 1954, vol. 35, p. 60-74.
Holland, "Generation and Replication of Defective Viral Genomes", Virology 1990B 2nd Edition Chapter 6, p. 77-99.
Holland, "Defective Viral Genomes", Virology 1990A 2nd Edition Chapter 8, p. 151-165.
Huang et al. "Defective Viral Particles and Viral Disease Processes", Nature (Lond) 1970, col. 226, p. 325-327.
Dimmock, "Antiviral Activity of Defective Interfering Influenza Virus in Vivo", Viral and Other Infections of the Human Respiratory Tract. 1996, Edited by S. Myint and D.Taylor-Robinson. Published in 1996 by Chapman & Hall ISBN 0 412 60070 6, p. 421-445.
Neumann et al. "Generation of Influenza A Viruses Entirely from Cloned cDNAs". Proc. Natl. Acad. Sci. Aug. 1999, vol. 96, p. 9345-9350.
Rott et al. "Untersuchungen Uber Die Hamagglutinierenden-nichtinfektiosen Teilchen Der Inftuenza-Viren", Z. Naturforschg. 1961, 16 b, p. 310-321.
Carter et al. "Synthesis of RNA Segments 1-3 During Generation of Incomplete Influenza A (Fowl Plague) Virus", Archives of Virology 1982, vol. 73, p. 109-119.
Murphy et al. "Orthomyxoviruses", Fields Virology 3rd Edition 1996, Chapter 46, p. 1397-1445.
Von Magnus, "Propagation of the PR8 Strain of Inftuenza A Virus in Chick Embryos. I. The Influence of Various Experimental Conditions of Virus Multiplication", Acta. Pathol. Microbiol. Scand. 1951A, vol. 28, p. 250-277.
Von Magnus, "Propagation of the PR8 Strain of Influenza A Virus in Chick Embryos. II. The Formation of "Incomplete" Virus Following Inoculation of Large Doses of Seed Virus", Acta Pathol. Microbiol. Scand. 1951B, vol. 28, p. 278-293.
Von Magnus, "Incomplete Forms of Influenza Virus", Adv. Virus Res. 1954, vol. 21, p. 59-79.
Von Magnus, "The in Ovo Production of Incomplete Virus by B/Lee and A/PR 8 Inftuenza Viruses", Arch. Virol. 1965, vol. 17, p. 414-423.
Carter et al. "Incomplete Avian Influenza Virus Contains a Defective Non-Interfering Component", Archives of Virology 1982, vol. 71, p. 13-25.
Clements, "Surface Warfare Against Pathogens Using Mucosal Vaccines", Nature Biotechnology Jul. 1997, vol. 15, p. 622-623.
Walker, "New Strategies for Using Mucosal Vaccination to Achieve More Effective Immunization", Vaccine 1994, vol. 12, No. 5, p. 387-400.
Cane et al. "Intracellular Stability of the Gene Encoding Influenza Virus Haemagglutinin", Virology 1990. vol. 175, p. 385-390.
Duhaut et al. "Heterologous Protection of Mice from a Lethal Human H1N1 Inftuenza A Virus Infection by H3N8 Equine Defective Interfering Virus: Comparison of Defective RNA Sequences Isolated from the D1 Inoculum and Mouse Lung", Virology 1998, vol. 248, p. 241-253.
Subbarao et al. "Evaluation of a Genetically Modified Reassortant H5N1 Influenza A Virus Vaccine Candidate Generated by Plasmid-Based Reverse Genetics", Virology 2003, vol. 305, p. 192-200.
Karber, "Statistical Methods in Virology", Textbook of Virology 5th Edition 1968, Chapter 8, Section 1, p. 104 and p. 118.
Von Magnus, "Studies on Interference in Experimental Inftuenza", Ark. Kemi. Mineral. Geologi. vol. 24N, No. 7, p. 1-6, (1947).
Mcghee et al. "The Mucosal Immune System: from Fundamental Concepts to Vaccine Development", Vaccine 1992, vol. 10, No. 2, p. 75-88.
Cane et al. "Intracellular Stability of the Interfering Activity of a Defective Interfering Influenza Virus in the Absence of Virus Multiplication", Virology 1987, vol. 159, p. 259-264.

* cited by examiner

ANTI-VIRAL PROTECTION WITH VIRUSES CONTAINING DEFECTIVE GENOME SEGMENTS

CROSS REFERENCE TO RELATED APPLICATIONS

This is the U.S. National Stage of International Application No. PCT/GB2009/051666 filed Dec. 8, 2009, which was published in English under PCT Article 21(2), which in turn claims the benefit of which in turn claims the benefit of Great Britain Application No. 0822672.2, filed Dec. 12, 2008.

FIELD OF THE INVENTION

The invention relates to virology and the prevention and/or treatment of viral infection and disease in animals, including birds and humans. The invention relates to the field of antiviral treatments. The invention further relates to methods of stimulating innate immunity and natural interferon production in humans or animals and in component parts of humans or animals, including cells and tissues. The invention also relates to the field of defective interfering (DI) viruses, including cloned DI viruses.

BACKGROUND TO THE INVENTION

The Orthomyxoviridae is a family of RNA viruses which infect vertebrates. The family includes those viruses which cause influenza.

Influenza is a viral infection of the respiratory system characterized by fever, cough, and severe muscle aches. There are three genera of influenza virus, identified by antigenic differences in their nucleoprotein and matrix protein: Influenzavirus A, Influenzavirus B and Influenzavirus C.

Influenza A and B viruses each contain eight segments of single stranded RNA (ssRNA). The viruses comprise major external virion proteins, haemagglutinin (HA) and neuraminidase (NA). The Influenzavirus A genus comprises 16 HA subtypes and 9 NA subtypes which probably form all 144 possible permutations. However, influenza B is a single subtype and is significantly distinct from influenza A.

Influenza C virus contains seven segments of ssRNA, because the virus lacks a separate neuraminidase gene (see Lamb, R. and Krug, R. M. (1996) Chapter 45; Orthomyxoviridae: The viruses and their replication—Fields Virology, 3$^{rd}$ Edition, Raven Publishers, Philadelphia).

Members of the family Paramyxoviridae are viruses with a narrow specific host range in nature, but in cultured cells they display a broad host range. Features of infection in vivo include the formation of inclusion bodies and syncytia. Paramyxovirus infection typically begins in the respiratory tract and may remain at that site (e.g., human respiratory syncytial virus, HRSV) or may spread to secondary sites (e.g., lymphoid and endothelial tissues for measles virus (MeV)). In general, paramyxovirus infections are limited by, and eliminated by, host immunity. However, virus sometimes can be shed for periods of weeks or months in normal and, especially, in immunocompromised individuals.

A genus within the Paramyxoviridae is Pneumovirus. This genus includes bovine respiratory syncytial virus (BRSV) and human respiratory syncytial virus (HRSV) of which there are two subtypes designated A and B and several virus strains e.g. HRSV strain A2, HRSV strain RS-S2 and BRSV strain Snook. There is also a murine pneumonia virus (also known as pneumonia virus of mice: PVM)

Antiviral drugs are a class of medication used specifically for treating viral infections. Specific antivirals are frequently used for specific viruses. Most of the antivirals now available are designed to help deal with HIV, herpesviruses (best known for causing cold sores and genital herpes but actually causing a wide range of diseases), the hepatitis B and C viruses (which can cause liver cancer), and influenza A and B viruses. Researchers are now working to extend the range of antivirals to other families of pathogens.

For example, Amantadine and Rimantadine are effective against all influenza type A viruses, but not influenza type B viruses. Viruses that are resistant to these compounds are commonly found. Other anti influenza A and B virus include Zanamivir (Relenza®) and Oseltamivir (Tamiflu®). However, the effectiveness of these therapies is somewhat limited. Treatment has to be started soon after infection and it needs to be given twice daily. Antiviral treatment is only able to shorten the duration of symptoms by one to three days. Viruses that are resistant to Tamiflu are increasingly being found in patients with influenza.

Vaccines are used to generate an immune response to attack viruses. Vaccines traditionally consist of a weakened or a killed version of the pathogen. More recently "subunit" vaccines have been devised that consist strictly of protein targets from the pathogen. Vaccines stimulate the immune system without doing serious harm to the host, and so when the real pathogen attacks the subject, the immune system responds to it quickly and blocks it.

Vaccines may be effective in combating infection by stable viruses, but are of limited use in treating a patient who, has already been, or is persistently, infected. Vaccines against rapidly mutating viruses, such as influenza, are problematic. The vaccine for influenza has to be updated each year. A vaccine against HIV, for example, remains elusive.

Defective interfering (DI) viruses have a long history. They were discovered as auto-interfering elements in influenza A virus preparations by von Magnus who studied them in the late 1940s and early 1950s (e.g. von Magnus, P (1947) Ark. Kemi. Mineral. Geol, 24b: 1). For many years these interfering elements were named after him. Later, when it was realized that these elements were found almost universally amongst viruses, they were called DI viruses (see e.g. Huang & Baltimore (1970) Nature 226: 325-327). Interest in DI viruses reached a peak in the 1970s but then waned due to an over-extravagant expectation of their in vivo antiviral activity.

All influenza A viruses have a replication apparatus that allows the exchange of genome segments (reassortment) in dually infected cells, giving these viruses immense genetic flexibility. Such an event gave rise to the 1957 and 1968 pandemic influenza viruses. In addition to the normal replication process, mistakes in replication occur that give rise to small RNAs of 400-500 nucleotides (nt) lacking around 80% of the central sequence of the template, which appears to result from the polymerase copying the initial part of the template, detaching from the template and then rejoining and copying the other terminus. These small RNAs retain the terminal replication and encapsidation signals. Their small size suggests that more copies can be made in unit time compared with the full-length RNA segment. Encapsidation of genomic RNAs appears to be an organized process so that a virion contains just one copy of each of the 8 segments. A virion does not appear to discriminate between a defective and a full-length RNA, so when defective RNAs are in excess they are encapsidated more frequently than the intact genome segment which they replace. A particle containing the deleted genome segment cannot synthesize the viral protein(s) normally encoded by that RNA, and is non-infectious, although it can be replicated in trans when that cell is infected by an influenza A virus. Incorporation of defective RNAs into virions results in a reduction in the amount of infectious virus produced. Thus virions carrying a deleted genome were known as interfering or defective-interfering (DI) viruses.

Viruses of the Orthomyxoviridae family give rise spontaneously to defective RNA segments as a result of an internal deletion (75-80% of the nucleotides) in one or more genomic segments. The DI virus genome is therefore a deleted form of the genome of the infectious virus which gave rise to it; and it has several unique properties which distinguishes it from other types of defective viral nucleic acid molecules (see Dimmock, N. J. (1996) "Antiviral activity of defective interfering influenza virus in vivo"—Viral and other infections of the human respiratory tract; S. Myint and D. Taylor-Robinson (Eds.), Chapman & Hall).

Compared to an active, i.e. live or infectious virus, a DI virus, while able to infect a cell, replicates and is propagated only when its genome is present in a cell which has been infected by a virus with a complete genome (sometimes referred to as a "helper virus"). DI influenza virus is encapsidated into virus particles which are usually indistinguishable in size and protein composition from infectious helper virus particles.

After arising, de novo, a DI genome is rapidly amplified in concentration relative to that of the genome of the infectious virus, so that within a few infectious cycles (or passages) there is more DI virus in a population than infectious helper virus.

DI virus has the ability to interfere intracellularly with infectious helper virus so that it is specifically able to inhibit multiplication of infectious helper virus.

In vivo animal studies have shown that spontaneously produced DI influenza A virus (A/equine/Newmarket/7339/79 (H3N8)) can, in sufficient amount, protect mice against lethal influenza A challenge with both the homologous virus (EQV) or with heterologous subtypes A/WSN (H1N1) or A/PR/8/34 (H1N1). In these studies the DI virus preparation was UV-treated in order to inactivate the infectivity of any live helper virus present. This amount of UV irradiation does not inactivate the interfering or protecting activity of the DI virus. A single administration appeared to provide prophylaxis for up to about 5 days. However, these DI influenza A virus preparations were heterogeneous and comprised a multiplicity of undefined defective RNA sequences from different genomic segments (see Noble and Dimmock (1994) Journal of General Virology 75: 3485-3491).

DI influenza A virus A/WSN (H1N1) grown in embryonated chicken's eggs protected mice against lethal challenge with A/WSN (H1N1). Comparison of egg-grown DI virus RNA species with DI virus RNA extracted from surviving mouse lungs showed that there were at least 5 putative DI RNA sequences present. Each of the five RNA species of the DI virus had an internal deletion (see Noble & Dimmock (1995) Virology 210: 9-19). The 3' and 5' ends of four of these RNA molecules appeared intact.

Duhaut & Dimmock (2000, Virology 275: 278-285) modified a defective segment 1 RNA of EQV by placing it under the control of a human RNA polymerase I promoter (Pol I) in a plasmid. Each of the plasmids encodes RNA of approx 400 nucleotides but, due to the exact position of the internal deletion, differing lengths of the 5' and 3' end sequences remained. Vero cells were transfected with each plasmid together with plasmids encoding the influenza virus PB1, PB2, PA, and NP proteins and the cells were then infected with one of three different helper virus subtypes, including the parent (H3N8) or an H2N2 or H1N1 subtype. Serial passage was carried out in cell culture. At least 150 nucleotides at the 5' end of the DI virus RNA were found to be necessary for reliable passage in vitro in each of the cell lines used together with the particular helper viruses used.

It has not been possible to experimentally elucidate the process by which non-cloned DI influenza A viruses reduce the yield of infectious virus, inhibit virus-induced cytopathology, and protect animals from clinical disease, as most populations of DI influenza A virus contain many different defective RNA sequences, derived from different genome segments and with a variety of central deletions. Thus the RNA content of such non-cloned populations of defective virus cannot be reproduced effectively, and it has not been possible to analyse the relationship between RNA sequence and antiviral activity.

Duhaut & Dimmock (2002, J. Gen. Virol. 83: 403-411) demonstrated that a DI influenza A virus RNA derived from a plasmid system appears to behave authentically in cell culture. One plasmid (POLI-317) gave rise to DI virus RNA that replicated stably in vitro in the presence of helper virus and strongly inhibited the production of the helper virus in that system.

Duhaut & Dimmock (2003, Journal of Virological Methods 108: 75-82) described the preparation of a defined (i.e. molecularly cloned) DI influenza A virus generated entirely from plasmids which were used to transfect host cells in culture. The plasmids used encoded the DI RNA (H3N8 or H7N7) and infectious influenza virus (A/WSN, H1N1). DI influenza A virus generated in this way was passaged once in embryonated chicken's eggs and then administered to mice in the presence of helper virus (H1N1). The cloned DI virus propagated intact within mouse lung. The cloned DI virus (without infectious helper) was also tested for any protective effect in mice against a lethal (H1N1) challenge. Some very weak and short lived prophylactic effect was observed, but this only delayed the onset of clinical symptoms and death in the mice.

Noble et al. (2004, Vaccine 22: 3018-3025) reported an in vivo study in mice using a naturally occurring (i.e. heterogeneous and undefined) DI influenza A virus preparation (EQV H3N8). Administration of this DI virus preparation to mice was found to generate prophylaxis protection for a period, and at the same time converted an otherwise lethal infection into an avirulent and immunizing infection.

Dimmock & Marriott (2006, Journal of General Virology 87: 1259-1265) described an apparent anomaly in which a heterogeneous and undefined DI influenza A virus preparation solidly protects mice from lethal disease caused by A/PR/8/34 (H1N1) and A/WSN/40 (H1N1) viruses, but only marginally protects from disease caused by A/Japan/305/57 (A/Jap H2H2). A/Jap was found to require 300-fold more infectious units to cause clinical disease in mice than A/PR8. The proportions of DI virus and challenge virus were varied and tested. A conclusion reached was that the efficacy of the DI virus depends on the infectious dose of challenge virus rather than its disease-causing dose.

Mann et al. (2006, Vaccine 24, 4290-4296) tested heterogeneous and undefined DI A/EQV RNAs that had been rescued by A/PR8 in ferrets. DI influenza A virus was administered in two doses followed by challenge with infectious A/Sydney 5/97 (H3N2). The DI virus-treated ferrets showed only occasional and mild clinical symptoms, compared to the control animals which became severely ill.

US2006/0057116 A1 (Kawaoka and Neumann) describes plasmids and a method of transfecting and culturing cells to produce recombinant influenza A virus in vitro in the absence of any helper virus. Specifically, influenza A viruses can be prepared entirely from their cloned cDNAs in transfected cell lines. Mutations can be incorporated into any gene segment.

WO2006/051069 (Solvay Pharmaceuticals and Erasmus University) discloses conditionally defective influenza virus particles and a method of making them. From the starting point of transfected cells not being able to produce large quantities of defective influenza virus particles for use as vaccines, the specification teaches an alternative method. The method involves a cell transfected with plasmids encoding seven RNA segments of the influenza virus but missing an eighth segment that expresses a polymerase protein. The cell includes a second expression plasmid carrying the sequence of the missing polymerase gene. On expression, the transfected cell yields "conditionally" defective virus particles which can only replicate in a cell line expressing the polymerase protein gene that is not present in the defective genome. The defective influenza virus particles can only replicate once in suitable, albeit not complemented, host animals or cells. The conditionally defective virus particles are intended for vaccine use or gene delivery purposes and so advantageously the virus particle preparations are unable to replicate in normal cells and contain no wild-type or helper virus.

Although a prototype system has been described (see Duhaut & Dimmock, 2003 supra) for preparing a cloned DI influenza A virus (which turned out to be only weakly protective on one occasion in mice), it does not offer a practical route for preparing the necessary amounts of cloned DI viruses needed for further laboratory investigations, let alone the amount of cloned DI virus that would be needed on a routine basis in order to carry out animal and human clinical trials or provide for prophylaxis and/or therapy in routine, epidemic or pandemic situations.

Huang, A. S. & Baltimore, D. (1970) "Defective viral particles and viral disease processes" *Nature* (*Lond*) 226, 325-327. This review article at page 325 describes how the synthesis of DI particles by cells or animal tissues on infection with high multiplicities (or undiluted passage virus) is achieved for Rift Valley fever virus, vesicular stomatitis virus, fowl plague virus, simian virus 40, polyoma virus, lymphocytic choriomeningitis virus, Sendai virus, simian virus 5, and poliovirus.

Holland, J. J. (1990) "Defective viral genomes" In *Virology,* 2nd edn. pp. 151-165. Edited by B. N. Fields & D. M. Knipe New York: Raven Press. In this review article, page 155 describes how serial undiluted passage of virus in cell culture (or eggs or animals) is still the method of choice for generation of DI particles of any virus.

Nayak, D. P., Chambers, T. M. & Akkina, R. K. (1985) "Defective-interfering (DI) RNAs of influenza viruses: origin, structure, expression and interference" *Current Topics in Microbiology and Immunology* 114, 103-151 is a review article which attests to the production of DI viruses by serial independent undiluted passage of virus.

WO2007/135420 (University of Warwick) describes a method of producing previously unavailable and sufficient quantities of cloned DI influenza A virus for experimental or clinical use in preventing or treating influenza A infection in humans or animals, including birds. Also described is the medical use of cloned DI influenza A as a prophylactic or therapeutic treatment of influenza A infection. The cloned DI influenza A virus is identified as having an antiviral effect on the same or different strains of infectious influenza A.

There is a continuing need to provide antiviral treatments against the range of virus infections in humans and animals, particularly against viruses where there are no existing antiviral treatments available, against viruses that exhibit rapid mutation or against viruses which may become resistant to existing antiviral medicaments and against newly discovered or poorly characterised viruses.

The inventors have made an unexpected discovery which is that cloned human DI influenza A virus protects against infection by a different (heterologous) virus. More particularly, the inventors have found that human DI influenza A virus protects mice subjected to a lethal challenge of pneumonia virus of mice (PVM). The inventors have also surprisingly discovered that cloned DI influenza A virus is capable of protecting mice against lethal challenge with infectious influenza B virus. This is an unexpected finding because, although influenza A and B viruses belong to separate genera within the same family of viruses, they do not interact genetically.

The inventors made a further, unexpected discovery which is that cloned DI influenza A virus administered to mice results in a stimulation of natural interferon production. Without wishing to be bound by any particular theory, the inventors believe that a mechanism by which cloned DI viruses may exert their antiviral effect against heterotypic viruses is by stimulating the localised production of natural interferon at the site of cloned DI virus administration.

Accordingly, in one aspect the present invention provides cloned, defective interfering (DI) virus for use in the prevention or treatment of virus infection or disease in an individual, wherein the infection or disease is caused by a virus which is different to the virus from which the DI virus is derived.

Cloned DI viruses included those which have single stranded RNA, as well as those which are double stranded RNA, single stranded DNA or double stranded DNA.

In another aspect the invention provides cloned, defective interfering (DI) influenza A virus for the prevention or treatment of an infection or disease caused by a virus other than influenza A.

A virus different to the virus from which the DI virus is derived is preferably a wild type strain of another virus. For example if the DI virus is DI influenza A virus, then the different virus is human respiratory syncytial virus (HRSV).

Cloned DI virus materials for use in the invention are preferably substantially uniform in terms of DNA or RNA nucleic acid sequence. The uniformity may be more than a percentage in the range 95-99.9% and 100% genetic uniformity, as measured by sequence % identity, may be provided.

Preventative (prophylactic) and therapeutic treatments (i.e. post infection when clinical symptoms are manifest) are possible within the scope of the invention. Therapeutic treatment may be administered when a suspected viral infection is still sub-clinical.

The infection or disease to be prevented or treated in accordance with the invention may be one caused by a respiratory or a systemic virus.

Such infection or disease may be caused by a virus of the Paramyxoviridae, such as a Pneumovirus, e.g. human respiratory syncytial virus (HRSV).

The infection or disease may be caused by a Metapneumovirus, e.g. human metapneumovirus (HMPV).

In other aspects of the invention the infection or disease may be caused by a virus of the Orthomyxoviridae, such as influenza B virus or influenza C virus.

In further aspects of the invention, the infection or disease may be caused by a hepatitis virus or a virus of the Hepadnaviridae, e.g., hepatitis B virus (HBV).

The infection or disease may be caused by a virus of the Flaviviridae, e.g. Hepacivirus. The virus may be hepatitis C virus (HCV).

In yet further aspects of the invention, the infection or disease may be one caused by Papillomaviridae, e.g. papillomavirus.

The virus causing the infection or disease can be one infectious against humans and other animals (including birds, reptiles or amphibians).

In accordance with the invention, cloned DI virus may be administered via the nose and/or via the lungs of an individual human or animal. Alternatively, the cloned DI virus may be administered parenterally, e.g. subcutaneously, intramuscularly, intravenously or intraperitoneally.

The invention also provides a method of stimulating innate immunity and natural interferon production by a cell, tissue, organ, or in a human or in an animal, comprising administering an interferon-inducing amount of a defective interfering (DI) virus to the cell, tissue, organ, human or animal, provided that the DI virus is not an RNA virus with a "copyback" or "snapback" RNA structure when DI virus is administered to a cell in cell culture.

In such methods of the invention, the DI interfering virus is preferably other than a DI vesicular stomatitis virus or DI Sendai virus when DI virus is administered to a cell in cell culture.

The stimulation of natural interferon production is readily measured by the person of skill in the art using known assays. The interferon produced may be of any of the naturally inducible type I interferons; namely interferon (IFN) type I and mainly IFN-$\alpha$ and IFN-$\beta$ (Theofilopoulos, A. N., Baccala, R., Beutler, B. and Kono, D. H. 2005 Type I interferons ($\alpha/\beta$) in immunity and autoimmunity. Annual Review of Immunology 23, 307-336).

In stimulating innate immunity and natural interferon production in accordance with the invention, the DI virus is preferably a cloned DI virus. More particularly the stimulation of natural interferon may employ a host replication competent helper virus. In further such embodiments the cloned DI virus may be a different strain of virus or may be heterotypic in relation to the helper virus.

When stimulating interferon production, then administration of DI virus needs to take place in advance of the desired antiviral effect. This is because there is a lag between administration and the reaction of the body whereby cells generate interferon. Normally a lag of 24 hours is seen and so administration is preferably about 24 hours or more prior to the desired level of interferon production.

The invention therefore also includes a method of preventing or treating a viral infection in an individual human or animal comprising administering an interferon-inducing amount of a defective interfering (DI) virus to the individual.

In such aspects of the invention, DI virus is preferably administered via the nose and/or via the lungs of the individual, although parenteral, e.g. subcutaneous, intramuscular, intravenous or intraperitoneal administration is possible.

In accordance with the aforementioned methods of the invention, DI virus may not be given directly to an individual, but additionally or alternatively, cells, tissue or organ may be isolated from the human or animal body, i.e. ex vivo and/or in vitro, treated with the DI virus in order to induce interferon production, and then reintroduced or transplanted back into the body of the same or another receptive individual or the same or similar blood or tissue type.

In accordance with all aspects of the invention defined above, the DI virus may be a DI influenza virus, preferably a DI influenza A virus, or a DI Semliki Forest virus.

The inventors therefore provide antivirals and antiviral treatments based on defective interfering viruses that have the capability of protecting against heterotypic (i.e. different) virus infection in any host. For example, in treating pulmonary viral infections, the antiviral medicament is preferably delivered by intranasal administration to the cells of the respiratory tract. Other routes of administration may include mucosal, pulmonary and oral cavity. Other routes include gastro-intestinal via oral administration.

An advantage of cloned DI virus is that an individual known or suspected of being infected with any virus can be treated for the infection, even if symptoms of infection have yet to be observed or infection diagnosed. The individual can be administered with the cloned DI virus medicament as soon as possible when an infection is suspected. Individuals can also be treated as soon as possible after having been in contact with other individuals of the same or different species and who are known or suspected to be infected with the virus. Advantageously, protection is not believed to involve an adaptive immune response and is achieved on administration of the cloned DI virus medicament alone without the need for administration of infectious helper virus. There is therefore no requirement to administer the cloned DI virus in advance of infection like a conventional vaccine (which relies on B cell and T cell-directed immune responses in order to generate a protective effect), although 24 hours pretreatment with DI virus is advantageous.

Medicaments in accordance with the invention may be administered to individuals on a precautionary basis.

The individual to which the medicament may be administered may be an animal or human, preferably wherein the animal is selected from a pig, horse, dog, cat or bird (wild or domesticated). In the case of birds, whether wild or domestic, the medicament may be administered conveniently via the oral tract, e.g. by incorporating the medicament in drinking water or in food. In the case of bird species, preferred domesticated species include, for example, duck, goose, turkey, or hen e.g. broiler chicken.

A dosage regime in accordance with the invention may consist of a single dose of medicament. The amount of cloned DI virus in a medicament can be measured by quantitative RT-PCR. Probes and/or primers specific for the deleted RNA or DNA segment are employed.

The amount of cloned DI virus in a medicament may be of the order (per dose) of 1 ng-10 μg of virus (measured in terms of total virus protein). The amount of DI virus may be in the range 0.05 μg-10 μg. Preferred embodiments include 0.01-0.1 μg, 0.01-1 μg or 0.01-10 μg of virus protein, more preferably 10 ng, 100 ng, 1 μg or 10 μg virus protein.

Where cloned DI influenza A virus is used as the basis of a medicament in accordance with the invention, the amount of cloned DI virus in the medicament may be in the range per dose of 0.05-5000 HAU, preferably a range selected from 0.1-100, 0.5-50 or 1-10 HAU. Other possible ranges include 0.05-10 HAU, 0.1-50 HAU, 1-100 HAU and 1-5000 HAU.

The amount of cloned DI virus, whether measured in terms of HAU or μg virus protein per dose, may be varied according to the subject. For example, a horse may require 4× the human dose, whereas a bird may require 1/10 of the human dose.

The defective nucleic acid in cloned DI virus may have at least one deletion compared with the genomic segment from which it derived, although a multiplicity of deleted portions of segment 1 may occur. The deletions may be separated by a multiplicity of contiguous nucleotides. The sequence of the defective nucleic acid may contain one or more nucleotide changes compared with the genomic segment from which it derived. These may comprise a different replacement nucleotide, a deleted nucleotide or an inserted additional nucleotide.

The 5' and 3' ends of the genomic segment including the deletion are preferably intact. In a more preferred embodiment the segment is segment 1. The effect of deletion is that the 5' end of the segment of virion RNA has at least 150, 200 or 220 nucleotides. Preferably the 5' end of the segment has a number of nucleotides in the range 150-500, more preferably 150-250, or 150-220.

In terms of the 3' end, the remaining (undeleted) portions comprise at least 20, 50, 100, 200, 300, 400 or 500 nucleotides. The 3' end of segment 1 may have a number of (undeleted) nucleotides in the range 20-600, 30-550, 40-500, 50-450, 60-400 or 75-250.

The segment deletion may be at least 50% of the nucleotides, preferably at least 75%, more preferably at least 80% of the nucleotides. In order for an effective deletion in the RNA segment, at least one nucleotide may be deleted. In more preferred embodiments, the deletions may consist of at least 3, 5, 10, 15, 20, 25, 50, 75, 100, 150, 200, 250, 300, 400, 500, 750, 1000, 1500, 3000 or 5000 nucleotides, preferably contiguous nucleotides. A multiplicity of deletions is possible within the same RNA segment.

The invention therefore provides a pharmaceutical composition comprising a cloned DI virus as hereinbefore described.

Pharmaceutical compositions of the present invention, suitable for administration, comprise the DI virus, in sterile aqueous or non-aqueous solutions, suspensions, and emulsions. The compositions may further comprise auxiliary agents or excipients, as known in the art, see, e.g., Berkow et al., The Merck Manual, $16^{th}$ edition Merck & Co., Rahman, N.J. (1992), Avery's Drug Treatment: Principles and Practice of Clinical Pharmacology and Therapeutics, 3rd edition, ADIS Press, Ltd., Williams and Wilkins, Baltimore, Md. (1987) & Osol (ed.), Remington's Pharmaceutical Sciences, Mack Publishing Co., Easton, Pa. 1324-1341 (1980). The composition of the invention is preferably presented in the form of individual doses (unit doses).

Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, e.g. purified water. As well as inert diluents, exemplary compositions may also include adjuvants, wetting agents, emulsifying and suspending agents, or sweetening, flavouring, or perfuming agents.

When a composition or medicament of the present invention is used for administration to an individual, it may further comprise salts, buffers, or other substances which are desirable for improving the efficacy of the composition.

Preferred compositions or medicaments are for mucosal delivery. Of the various mucosal delivery options available, the intranasal route is the most practical as it offers easy access with relatively simple devices that have already been mass produced. The composition of the invention is thus preferably adapted for and/or packaged for intranasal administration, such as by nasal spray, nasal drops, gel or powder (see Almeida & Alpar (1996) J. Drug Targeting 3: 455-467 and Agarwal & Mishra (1999) Indian J. Exp. Biol. 37: 6-16.).

Other possible routes for mucosal delivery include oral, intragastric, pulmonary and intestinal. The composition of the invention may be adapted for and/or packaged for mucosal administration (e.g. see Walker (1994) Vaccine 12: 387-400, Clements (1997) Nature Biotech. 15: 622-623 & McGhee et al. (1992) Vaccine 10: 75-88). For oral administration tablets or capsules (optionally enteric-coated), may be provided.

Optionally, liquid, transgenic plant material, drops, inhaler, aerosol, enteric coating, suppository, pessary, etc. (see Michetti (1998) J. Gastroenterol. [Suppl X]: 66-68 and chapter 17 of Vaccine design: the subunit and adjuvant approach, eds. Powell & Newman, Plenum Press 1995).

The composition of the invention may be administered by a parenteral route. The parenteral route includes intravenous, intramuscular, subcutaneous, intradermal, epicutantous/transdermal, or intraperitoneal administration. Various types of parenteral formulations may be used, including solutions, micellar dispersions, emulsions, inclusion complexes (cyclodextrins), liposomes and suspensions.

Whatever route of delivery is used, compositions or medicaments of the invention are preferably in unit dose form. Effective doses can be routinely established. For example, a typical human dose of the composition for injection or for intranasal use has a volume between 0.1-0.5 ml e.g. two 100 μl sprays, one per nostril.

Compositions of the invention are preferably sterile and preferably not pyrogenic. At higher concentrations, a DI influenza A virus composition may be pyrogenic or exhibit residual pyrogenic activity. The compositions are preferably buffered, e.g. at between pH 6.5 and pH 8, generally around pH 7.

An advantageous form of nasal administration is described in WO2006/041819 (Medimmune).

The invention also includes a method of converting a virulent virus infecting a subject into an avirulent virus infection, comprising administering to the subject an effective amount of a cloned DI virus.

The cloned DI virus particle may be administered before, simultaneously or after the infection.

The invention includes a method of converting a virulent virus infecting a subject into an avirulent virus infection that vaccinates the subject against the infecting virus, comprising administering to the subject a cloned DI influenza A virus.

The subject may, or may be suspected of being, infected with a given virus. In cases of actual or even suspected infection, cloned DI virus may be administered as soon as possible, within 48 hours, preferably within 24 hours of the individual being infected, or being suspected of being infected. Similarly, individuals can be administered the cloned DI virus as a precautionary measure if they are shortly to be exposed to infectious virus, whether from infected humans, animals or birds. Persons having to deal with animal or bird carcasses or with human corpses known or suspected of being infected with pathogenic viruses, particularly in epidemic or pandemic situations can be administered the cloned DI virus of the invention. Such persons can be administered the medicament of the invention on a precautionary basis immediately prior to risk of virus exposure. Unlike the employment of a vaccine, it is not necessary to know the identity of the infecting virus.

In each of the methods of the invention described above, the cloned DI virus is administered in sufficient amount. The helper virus may be of any corresponding strain of the virus, whether from humans or other animals, including birds.

Cloned DI virus also protects when given up to 24 hours after infection and beyond. It is thus able to counter an actual infection. It can therefore also be used as a treatment for family and other direct contacts of infected individuals.

Cloned DI virus is easy to administer. A drop of saline containing the cloned DI virus can simply be squirted up the nose. Aerosol administration, used already for some vaccines, offers another simple route of administration. The cloned DI virus provides a useful treatment for domestic animals, e.g. via drinking water.

The invention will now be described in detail with reference to Examples and to the drawings in which:

FIG. 1 is a photograph of a gel showing RT-PCR of 244 RNA contained in allantoic fluids of eggs inoculated with mixtures of influenza A DI 244/PR8 and infectious influenza B as described in Tables 1 and 2. M=DNA marker; A=1/10 DI+B/Lee; B=1/100 DI+B/Lee; C=1/1000 DI+B/Lee; D=1/10,000 DI+B/Lee; E=B/Lee; F=1/10 DI; G=saline.

Figure 1:
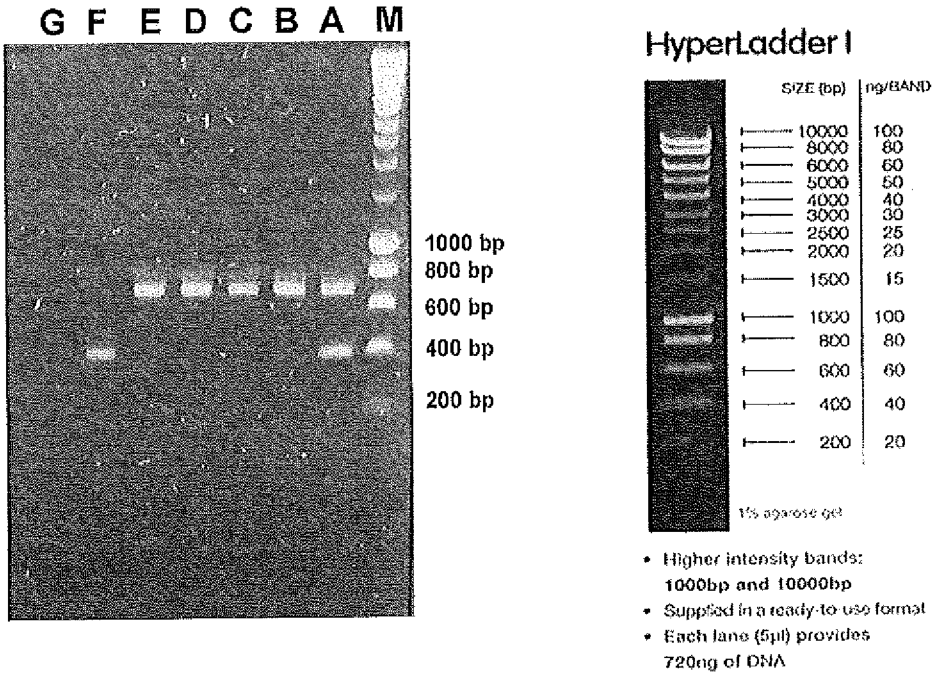

The inventors have carried out experiments and unexpectedly found that some influenza A DI viruses afford mice a degree of protection from influenza B infections. The order of efficacy of DI viruses tested against influenza B was found to be:

244/*PR*8=220/*Vic*>220/*PR*8 i.e. 244/PR8 and 220/Vic and are more efficacious than 220/PR8.

Whereas the order of efficacy of DI viruses against influenza A (see Tables 1 and 2 below) is:

244/*PR*8>220*Nic*=317*Nic*>220/*PR*8 i.e. 244/PR8 and 220/Vic are the most efficacious against both influenza A and influenza B viruses and 220/PR8 is the least efficacious. Tests with 317/Vic are not complete.

However, when DI influenza A virus was administered 24 hours before infection with influenza B virus the order of efficacy of DI viruses against influenza B was found to be:

244/*PR*8>220/*PR*8 i.e. Under these conditions 244/PR8 is again the most efficacious and 220/PR8 the least efficacious.

TABLE 1

Summary of protection by 244/PR8 and 244/WSN DI influenza A viruses against A/WSN: the lowest effective dose is highlighted

| HAU/ Mouse | Virus protein/mouse | Dilution | 244/Pr8 793 | | 244/Pr8 797 | | 244/Pr8 804 | | 244/Pr8 812 | | 244/Pr8 813 | | 244/WSN 808 | |
|---|---|---|---|---|---|---|---|---|---|---|---|---|---|---|
| 4000 | 12 μg | 1/1 | 3477 | ++++ | 3563 | ++++ | Nd | | Nd | | 3903 | ++++ | Nd | |
| | | | 3528 | ++++ | | | | | | | | | | |
| 400 | 1 μg | 1/10 | 3487 | ++++ | 3563 | ++++ | 3640* | ++++ | 3704 | ++++ | 3885 | ++++ | 3667** | ++++ |
| | | | | | | | 3692 | ++++ | | | 3895 | ++++ | | |
| | | | | | | | | | | | 3903 | ++++ | | |
| | | | | | | | | | | | 3907 | +++± | | |
| | | | | | | | | | | | 3919 | ++++ | | |
| 40 | 120 ng | 1/100 | 3498 | ++++ | 3563 | +++ | 3640 | ++++ | 3704 | ++++ | 3718 | ++ | 3667 | ++++ |
| | | | 3512 | +++ | | | 3676 | ++++ | | | 3884 | ++ | 3676 | ++++ |
| | | | 3584 | +++± | | | 3687 | | | | 3895 | ++ | | |
| | | | | | | | | | | | 3903 | ++ | | |
| 4 | 12 ng | 1/1000 | 3512 | + | Nd | | 3640 | ++++ | 3704 | ++ | 3718 | - | 3667 | - |
| | | | | | | | 3676 | + | | | 3895 | ++ | 3676 | ± |
| 0.4 | 1 ng | 1/10000 | Nd | | Nd | | Nd | | Nd | | Nd | | 3667 | - |

793, 797, 804, 812 and 813 are all independent but equivalent preparations of 244/PR8.

*New titration of WSN: 640x;

**New dilution and titration of WSN: 640a.

Nd, not done.

TABLE 2

Summary of protection by 220/Vic, 220/PR8 and 317/Vic DI influenza A viruses against A/WSN: the lowest effective dose is highlighted

| | | | 220/Vic | | | | 220/PR8 | | 317/Vic | |
|---|---|---|---|---|---|---|---|---|---|---|
| HAU/mouse | Virus protein/mouse | Dilution | 792 | | 798 | | 794 | | 796 | |
| 4000 | 12 µg | 1/1 | 3415 | ++++ | 3588 | ++++ | 3511 | ++++ | 3517 | ++++ |
| | | | 3527 | ++++ | | | | | 3539 | ++++ |
| | | | | | | | | | 3554 | +++ |
| | | | | | | | | | 3890 | +++± |
| 400 | 1 µg | 1/10 | 3498 | ++++ | 3588 | +++ | 3511 | + | 3517 | +++ |
| | | | 3892 | +++ | | | | | 3812 | ++ |
| 40 | 120 ng | 1/100 | 3892 | - | 3588 | - | 3511 | + | 3517 | - |
| | | | | | | | | | 3812 | + |
| 4 | 12 ng | 1/1000 | Nd | | Nd | | Nd | | Nd | |
| 0.4 | 1 ng | 1/10000 | Nd | | Nd | | Nd | | Nd | |

Nd, not done.

Protection from influenza B was found to require 100-fold more DI influenza A than required to protect against influenza A infection (see Table 6). Influenza B has a similar $ID_{50}$:$LD_{50}$ to the influenza A viruses used, and so the low DI influenza A efficacy does not appear due to an excessively high dose of influenza B challenge virus.

It is unlikely that influenza A DI RNAs swamp the influenza B infection by the more rapid replication of the small DI RNA as influenza and B viruses are not known to interact genetically. For example, all attempts to make influenza A×influenza B hybrid viruses (reassortants) have failed. In addition the inventors have found that influenza B does not support the replication of influenza A DI RNA 244.

Active DI viruses have also been found to protect mice from B/Lee by the stimulation of alpha/beta interferons in the respiratory tract and the inventors have found that:

(a) DI influenza A protects mice from infection with the heterologous pneumonia virus of mice (PVM) in the mouse.

(b) Intranasal DI influenza A (with no infectious helper virus and no challenge virus) stimulates interferon in the lungs of mice, as demonstrated by in vitro antiviral bioassay.

A 1/100$^{th}$ of the dose of DI influenza A that protects mice from B/Lee also protects mice from influenza A. This suggests that interferon alpha/beta is not essential to protection from influenza A—this is corroborated by a finding that mutant mice that lack interferon alpha/beta activity (because they lack the interferon alpha/beta receptor) are protected from influenza A by DI influenza A.

In protecting mice against PVM, mice are inoculated with DI influenza A virus 24 h before the virus challenge. DI influenza A virus was equally effective against influenza B infection when inoculated 24 h before the virus challenge. However, when DI influenza A virus and influenza B virus were inoculated simultaneously, a 10-fold higher concentration of DI influenza A virus was required to effect the same degree of protection.

A few other DI viruses (vesicular stomatitis virus, a rhabdovirus and Sendai virus, a paramyxovirus) are known to stimulate interferon alpha/beta in vitro. However, these are all "snapback" RNAs—i.e. single stranded RNAs whose 3' and 5' halves are complementary (see Marcus, P. I. & Sekellick, M. J. (1977) *Nature* (*Lond*) 266, 815-819; Sekellick, M. J. & Marcus, P. I. (1982) *Virol* 117, 280-285; Marcus, P. I. & Gaccione, C. (1989) *Virol* 171, 630-633; Strahle, L., Garcin, D. & Kolakofsky, D. (2006) *Virol* 351, 101-111.

A range of other DI viruses other than influenza A DI viruses can be used to induce interferon in animals and cells. Preferably such DI viruses are cloned and are not "snapback" or "copyback". For example, there are various cloned DI viruses which belong to the Alphavirus genus of the family Togaviridae, and specifically to Sindbis virus and Semliki Forest virus (SFV). They are all similar in structure but differ in sequence. The SFV DI viruses have been tested for their ability to protect animals. The SFV DI viruses DI-6 and DI-19 have both been cloned [see Thomson, M. and N. J. Dimmock, *Common sequence elements in structurally unrelated genomes of defective interfering Semliki Forest virus*. Virology, 1994. 199: p. 354-365; Thomson, M., C. L. White, and N. J. Dimmock, *The genomic sequence of defective interfering Semliki Forest virus* (*SFV*) *determines its ability to be replicated in mouse brain and to protect against a lethal SFV infection in vivo*. Virology, 1998. 241: p. 215-223.] SFV has a single molecule of single stranded, positive sense RNA that comprises 11422 nt. The Alphaviruses are viruses of vertebrates that are insect-transmitted. They replicate in both the invertebrate and vertebrate hosts. Alphavirus DI viruses have been reviewed [see Kaariainen, L. and H. Soderlund, *Structure and replication of alphaviruses*. Current Topics in Microbiology and Immunology, 1978. 82: p. 15-69; Stollar, V., *Defective interfering alphaviruses*, in *The Togaviruses*, R. W. Schlesinger, Editor. 1980, Academic Press: New York. p. 427-457; Schlesinger, S. and B. G. Weiss, *Defective RNAs of alphaviruses*, in *The Togaviridae and Flaviviridae*, S. Schlesinger and M. J. Schlesinger, Editors. 1986, Plenum Press: New York and London. p. 149-169; Barrett, A. D. T. and N. J. Dimmock, *Defective interfering viruses and infections of animals*. Current Topics in Microbiology and Immunology, 1986. 128: p. 55-84; Dimmock, N. J., *The biological significance of defective interfering viruses*. Reviews in Medical Virology, 1991. 1: p. 165-176.3-7]. SFV DI-19 is 1244 nt long and has 10.9% of the virion genome. SFV DI-19 has no major double stranded region. In terms of biological activity, the DI-19 virus interferes in cell culture with SFV multiplication and RNA replication and protects mice from SFV-mediated disease. SFV is neurotropic and when mice are inoculated intranasally, the virus enters the brain probably by entering and ascending the olfactory nerve, and causes encephalitis and usually fatal disease. Co-administration of SFV DI-19 with SFV protects against such disease.

Many viruses give rise to defective genomes and many of such defective viruses will be interfering viruses. The following are given as a list of non-limiting examples of viruses where defective genomes may be found:

Family Herpesviridae
- Herpes simplex virus
- Equine herpesvirus
- Pseudorabies
- Cytomegalovirus
- Herpesvirus
- Epstein-Barr virus Family Papovaviridae
- SV40
- Papovaviruses
- Polyoma virus Family Baculoviridae
- Baculovirus Family Hepadnaviridae
- Hepatitis B virus
- Duck hepatitis B virus Family Adenoviridae
- Adenovirus type 12
- Mouse adenovirus Family Parvoviridae
- Parvoviruses In the examples below mice were used under the Home Office Project Licences PPL 40/2561 and PPL 40/2129 and Personal Licences 30/1253 and PIL 40/03497.

EXAMPLE 1

Demonstration that DI Influenza A Virus (244/PR8)-Mediated Protection of Mice from Infectious Influenza A Virus Does not Depend on the Induction of Interferon Type I An experiment was designed to determine if DI influenza A virus-mediated protection of mice from influenza A virus needs a functioning interferon type I system. An attempt was made to protect mutant mice that lack the type I interferon receptor. This receptor is used by all type I alpha and beta interferon proteins (13 alpha interferons and the 1 beta interferon).

Mice (wild type (129 Sv/Ev) or receptor null (129 Sv/Ev IFNα/βR−/−); Banting and Kingman Ltd, approximately 5 weeks-old) were infected intranasally under light anaesthesia with a mixture (40 μl) of influenza A/WSN (10 $LD_{50}$) mixed with DI influenza A virus 244/PR8 (400 HAU, 1.2 μg; #813). Five mice were used per infected group and two mice for the DI virus alone and diluent inoculated groups.

Tables 2 and 3 below show that most of the wild-type mice given virus and inactivated DI influenza A became ill, lost weight and died, whereas those given virus and active DI influenza A remained clinically well although their weight gain was less than that of the control DI or diluent inoculated mice during days 5-8.

TABLE 2

Percentage weight change in wild type mice inoculated intranasally with DI influenza A virus and infectious influenza A virus

| Days | iDI + V | DI + V | DI | Mock |
|---|---|---|---|---|
| 0 | 0 | 0 | 0 | 0 |
| 1 | 0 | 0 | 0 | 2.7 |
| 2 | 3.4 | 4 | 6.1 | 5.4 |
| 3 | 6.7 | 6.1 | 9.1 | 8.1 |
| 4 | 9 | 12.1 | 12.1 | 16.2 |
| 5 | 0 | 10.1 | 12.1 | 10.8 |
| 6 | −5.6 | 10.1 | 18.2 | 13.5 |
| 7 | −22.5 | 8.1 | 18.2 | 16.2 |
| 8 | −25.8 | 10.1 | 21.2 | 18.9 |

TABLE 2-continued

Percentage weight change in wild type mice inoculated intranasally with DI influenza A virus and infectious influenza A virus

| Days | iDI + V | DI + V | DI | Mock |
|---|---|---|---|---|
| 9 | | 13.1 | 24.2 | 16.2 |
| 10 | | 16.2 | 24.2 | 21.6 |
| 11 | | 20.2 | 27.2 | 27 |
| survivors | 20% | 100% | 100% | 100% |

TABLE 3

Clinical score in wild type mice inoculated intranasally with DI influenza A virus and infectious influenza A virus

| Days | iDI + V | DI + V | DI | Mock |
|---|---|---|---|---|
| 0 | 1* | 1 | 1 | 1 |
| 1 | 1 | 1 | 1 | 1 |
| 2 | 1 | 1 | 1 | 1 |
| 3 | 1 | 1 | 1 | 1 |
| 4 | 1.6 | 1 | 1 | 1 |
| 5 | 1.8 | 1 | 1 | 1 |
| 6 | 2.7 | 1 | 1 | 1 |
| 7 | 3 | 1 | 1 | 1 |
| 8 | 3.4 | 1 | 1 | 1 |
| 9 | 4.2 | 1 | 1 | 1 |
| 10 | 4.2 | 1 | 1 | 1 |
| 11 | 4.2 | 1 | 1 | 1 |
| survivors | 20% | 100% | 100% | 100% |

*1 = well, 5 = dead

Tables 4 and 5 below show that all the mice given virus and inactivated DI influenza virus became ill, lost weight and died. Of those given virus and active DI influenza A virus only a minority (2/5) showed any clinical disease and this was extremely mild and transient.

TABLE 4

Percentage weight change in interferon receptor-null mice inoculated intranasally with DI influenza A virus and infectious influenza A virus

| Days | iDI + V | DI + V | DI | Mock |
|---|---|---|---|---|
| 0 | 0 | 0 | 0 | 0 |
| 1 | 0 | −2 | 2.8 | 2.6 |
| 2 | 3 | 1 | 5.6 | 5.1 |
| 3 | −4 | 4.1 | 8.3 | 7.7 |
| 4 | −11.1 | 8.2 | 13.9 | 15.4 |
| 5 | −18.2 | −1 | 11.1 | 12.8 |
| 6 | −22.2 | −4.1 | 11.1 | 15.4 |
| 7 | −26.3 | −6.1 | 13.8 | 12.8 |
| 8 | | −3.1 | 16.7 | 15.4 |
| 9 | | 2 | 16.7 | 15.4 |
| 10 | | 6.1 | 19.4 | 18 |
| 11 | | 9.2 | 19.4 | 18 |
| Survivors | 0% | 100% | 100% | 100% |

TABLE 5

Clinical score in interferon receptor-null mice inoculated intranasally with DI influenza A virus and infectious influenza A virus

| Days | iDI + V | DI + V | DI | Mock |
|---|---|---|---|---|
| 0 | 1 | 1 | 1 | 1 |
| 1 | 1 | 1 | 1 | 1 |
| 2 | 1 | 1 | 1 | 1 |
| 3 | 1.8 | 1 | 1 | 1 |
| 4 | 2.6 | 1 | 1 | 1 |
| 5 | 3.8 | 1.2 | 1 | 1 |
| 6 | 4 | 1.4 | 1 | 1 |

TABLE 5-continued

Clinical score in interferon receptor-null mice inoculated intranasally with DI influenza A virus and infectious influenza A virus

| Days | iDI + V | DI + V | DI | Mock |
|---|---|---|---|---|
| 7 | 4.2 | 1.4 | 1 | 1 |
| 8 | 5 | 1.2 | 1 | 1 |
| 9 | | 1 | 1 | 1 |
| 10 | | 1 | 1 | 1 |
| 11 | | 1 | 1 | 1 |
| survivors | 0% | 100% | 100% | 100% |

*1 = well, 5 = dead

Mice lost weight briefly from days 5-7 and then recommenced weight gain from day 8. The controls gained weight throughout this period. The weight loss in mutant mice was greater than that seen in the parallel group of wild-type mice (DI+V).

The data show that DI influenza A virus substantially protects mice lacking a functioning type I interferon system from influenza A virus. However, a transient weight loss and very mild transient disease in some animals suggests that interferon type I may make a small contribution to the protection mediated by DI influenza A virus.

The same result was found in another experiment (data not shown).

EXAMPLE 2

Demonstration that Some DI Influenza A Viruses Protect Mice from Infection with Influenza B/Lee—Simultaneous Inoculation The original aim of a series of experiments was to use an influenza B virus as a negative control to show that the protecting activity of various defective interfering (DI) influenza A viruses in mice are specific in their protection against influenza A as opposed to other viruses. Surprisingly, DI influenza A 244/PR8 was found to have activity against influenza B, and DI influenza A was one of the most active of the DI viruses tested per unit of total viral HA. The possibility that the infecting dosage of influenza B was contaminated with influenza A virus is dismissed because Western blotting shows that the NP antigens of the influenza B and a known influenza A virus are unrelated.

The primary challenge virus was influenza B/Lee/40 #795. The identity of this virus was checked and confirmed as influenza B by its positive reaction with a standard antibody to influenza B NP protein. This antibody did not react with influenza A virus. Influenza A/WSN (H1N1) #640 was also used to confirm that a DI preparation was active. Both were used at 10 $LD_{50}$/mouse. Viruses were stored at −70° C. diluted in PBS containing 0.1% BSA (Sigma). Viruses were thawed at 37° C. and kept on ice until used, usually within 1-2 h.

For the DI virus, the RNA 1 DI RNA 220 was cloned at Warwick (see Duhaut, S. D. & Dimmock, N. J. (1998). *Virol* 248, 241-253; Duhaut, S. & Dimmock, N. J. (2000) *Virol* 275, 278-285; Duhaut, S. D. & Dimmock, N. J. (2002) *J Gen Virol* 83, 403-411; Duhaut, S. D. & Dimmock, N. J. (2003) *J Virol Meth* 108, 75-82.). The RNAs were incorporated as DI viruses (220/PR8, 220/Vic and DI influenza A (244/PR8) by transfection of cells with plasmids that produce infectious influenza A/PR/8/34 (H1N1) or A/Victoria/3/75 (H3N2). The full nomenclature is:

220/PR8=RNA1_220/445_A/equine/Newmarket 7339/79 (H3N8)×A/PR/8/34 (H1N1)

220/Vic=RNA1_220/445_A/equine/Newmarket/7339/79 (H3N8)×A/Victoria/3/75 (H3N2)

244/PR8=RNA1_244/395_A/PR/8/34 (H1N1)×A/PR/8/34 (H1N1)

Tissue culture fluid was passaged by the allantoic route in embryonated chicken's eggs to make a seed stock. Working stocks of DI influenza A viruses were grown by inoculating eggs with a constant amount of a seed stock (10 μl) in the same way. Eggs were incubated at 33° C. for 2 days. Allantoic fluids were collected and DI virus purified by differential centrifugation through sucrose. The resulting virus pellet was resuspended at $2\times10^5$ HAU/ml in PBS containing 0.1% BSA (Sigma) and kept in liquid nitrogen storage. The presence and integrity of DI RNA was confirmed by RT-PCR using specific primers and sequencing.

Various DI batches were used. DI virus was thawed at 37° C. until just melted and kept on ice until used, usually within 1-2 h. DI virus was UV-irradiated at room temperature at 254 nm for 40 seconds to remove helper virus infectivity (DI). An aliquot of the same material was UV-irradiated in the same way for 8 minutes to inactivate protecting activity (iDI). The latter retains full haemagglutinin and neuraminidase activities. UV irradiation was carried out in microtiter trays chosen so that there was a constant depth of approximately 1-2 mm regardless of the volume being irradiated:

6 well-plate for about 1000 μl 12 well-plate for about 350 μl 24 well-plate for about 200 μl.

Irradiation of virus infectivity was carried out using a UV strip light approximately 10 cm from the sample and the lamp was warmed up for a few minutes before use. Under the lamp is a cross used to align the wells with the lamp. The plates were agitated continuously by hand for 40 s and intermittently for 8 min. Duration of irradiation was determined empirically by irradiating infectious virus under conditions that mimic the irradiation of DI virus, and determining the residual infectivity. UV inactivation of influenza infectivity follows single hit kinetics and thus prediction can be made for any titre of virus. A log is kept of UV lamp use to ensure that the lamp is changed before its efficacy falls. Mice are routinely inoculated with DI virus (after 40 seconds of UV) alone to check that the inactivation was successful.

Inbred C3H/He-mg mice were supplied by the Small Animal Unit at the University of Warwick and were used at approximately 4-6 weeks' of age and 16-20 g. Both sexes were used having been shown to be equally susceptible to infection with influenza A virus. Mice were housed in single sex cages generally in groups of 4-6 animals at 19-23° C. and 45-65% relative humidity. Food and water were available continuously. Mice were not identified individually.

Mice were infected intranasally with virus after light ether anaesthesia, usually with 40 μl split between the 2 nostrils. Animals regain consciousness and start moving within a few seconds of inoculation. After infection mice are assessed daily, scored clinically and the group weight determined—both daily. A standard proforma was used (below). The clinical criteria used were as follows. When required these can be scored quantitatively on a 1-5 scale as follows:

1 point for each healthy mouse.

2 points for each mouse showing signs of malaise, including slight piloerection, slightly changed gait, and increased ambulation (abbreviated as 'sick' on the clinical assessment proforma).

3 points for each mouse showing signs of strong piloerection, constricted abdomen, changed gait, periods of inactivity, increased breathing rate, and sometime râles (abbreviated as 'sicker' on the clinical assessment proforma).

4 points for each mouse with enhanced characteristics of the previous group, but showing little activity, and becoming moribund; such mice were killed when it was clear that they would not survive (abbreviated to 'sickest' on the clinical assessment proforma).

5 points for a dead mouse.

In previous studies, infected mice that had been treated with DI virus showed no sign of disease or weight loss, but it was determined previously that such animals experienced a silent, sub-clinical infection which stimulated an adaptive immune response which protected them from a second challenge with a very large dose of the same virus. In order to determine the immune status of animals after treatment with DI virus, animals were challenged with infectious virus for a second time. This was B/Lee, given as already described, at 3 weeks after the first infection. The virus dose was approximately 10,000 $LD_{50}$.

Mice were inoculated intranasally with a mixture of DI influenza A virus and 10 $LD_{50}$ of challenge B/Lee or A/WSN or inactivated DI influenza A virus mixed with 10 $LD_{50}$ of challenge B/Lee or A/WSN.

Inactivated DI influenza A virus contains the same amount/activity of haemagglutinin and neuraminidase as active DI virus. Three weeks after the first B/Lee challenge, mice were rechallenged with a high dose of B/Lee to determine their immune status. Table 6 below summarizes the protection observed with the different DI influenza A viruses. What can be seen is that at 12 μg or 4000 HAU/mouse there is strong and reproducible protection with DI influenza A virus and 220/Vic, but no significant protection with 220/PR8. 220/Vic was protective using 1.2 μg DI virus per mouse. The level of DI influenza A virus protection from B/Lee is approximately 100-fold less than the protection it affords from A/WSN. The protection offered by DI influenza A virus against influenza A virus is significant at 120 ng.

The DI preparations protected against influenza A to differing extents (see Tables 1 and 2 above). This can be summarized as:

$$244/PR8>220/Vic>220/PR8$$

All DI influenza A virus preparations are standardized by HAU and the range in activity seen against influenza B is remarkable. The activity does not correlate with the DI RNA as 220/PR8 is active while 220/Vic is not. Nor does activity correlate with the helper virus as 244/PR8 is active while 220/PR8 is not.

TABLE 6

Protection of mice from influenza B/Lee using various cloned DI influenza A viruses. B/Lee was mixed with DI virus and administered simultaneously to mice by the intranasal route.

| | DI virus | | | | | | | | |
|---|---|---|---|---|---|---|---|---|---|
| | 244/PR8 | | | 220/Vic | | | 220/PR8 | | |
| Mass or dilution | Exp. | DI # | Protection | Exp. | DI # | Protection | Exp. | DI # | Protection |
| 12 μg or 1/1 | 3528 | 793[e] | ++++ | 3527 | 792 | ++++ | 3549 | 794 | –[a] |
| | 3584 | 793 | ++[b] | 3892 | 798 | +++[d] | 3808 | 794 | +[a] |
| | 3779 | 812 | +++ | | | | 4096 | 794 | +a |
| 1 μg or 1/10 | 3584 | 793 | ±[c] | 3892 | 798 | ++[d] | 3808 | 794 | –[a] |
| | 4192 | 813 | ++ | | | | | | |
| 120 ng or 1/100 | 3584 | 793 | – | 3892 | 798 | –[d] | | | |

A control in all experiments was inactivated DI virus mixed with B/Lee (data not shown). This gave no protection.

[a]No WSN positive control for protection was used in this experiment.

[b]This was a stronger challenge than usual: nonetheless DI influenza A delayed disease by 4 days although al (5/5) mice became ill, and only 1/5 died (compared with inactivated DI influenza A where 5/5 died on day 6). A positive control of 1/100 DI gave good protection from WSN.

[c]DI influenza A delayed disease but 4/5 died.

[d]No virus alone control in this experiment, so 1/100 DI + B/Lee that gave no apparent protection was used.

[e]Virus stock book reference number.

++++, indicates complete protection from disease and weight loss;

–, no protection compared with a virus alone, or virus + inactivated DI control;

+++, ++, +, ± are intermediate gradations of high to low protection respectively.

Infectivity per HAU of B/Lee

To check whether the relative insensitivity of influenza B to DI influenza A results from a high mouse infectivity ($MID_{50}$):$LD_{50}$ ratio, a titration of B/Lee was carried out in mice. The titration determined if mice were infected (and thus had acquired immunity) by challenging at 3 weeks after the first infection with a high dose of homologous virus. The $LD_{50}$ was determined in the usual way. There were only 20 $MID_{50}$/$LD_{50}$ (see #3846). This means that the infectious dose was only 20-fold higher than the lethal dose and well within the range of the influenza A viruses that are commonly use to challenge mice. Thus the dose of influenza B was not excessive.

Protected Mice Develop Adaptive Immunity

Mice that survived the first B/Lee challenge through administration of DI virus were protected from a second very high challenge with B/Lee, showing that they developed an adaptive immunity to B/Lee (data not shown).

EXAMPLE 3

Elucidating the Nature of DI Influenza A Virus-Mediated Protection of Mice from Infection with Influenza B Virus: Influenza B Virus does not Replicate Influenza A DI RNA 244

Influenza type A and type B viruses are not known to interact genetically, although both have genomes composed of 8 segments. Different influenza A viruses undergo genetic reassortment of their RNA segments and likewise different influenza B viruses undergo genetic reassortment of their RNA segments. The only suggestion of any interaction comes from an in vitro experiment in which influenza A replicated an influenza B HA gene linked to a CAT reporter [Jackson, D., A. Cadman, T. Zurcher, and W. Barclay, *A reverse genetics approach for recovery of recombinant influenza B viruses entirely from cDNA*. Journal of Virology, 2002. 76: p. 11744-11747.1]. However, the inventors are not aware of an ability of an infectious influenza B virus to replicate influenza A defective-interfering (DI) RNA in vivo or vice versa.

In order to determine if infectious influenza B virus replicates DI RNA 244 present in influenza A 244/PR8 in embryonated eggs, RT-PCR was used to look for an increase in the amount of RNA 244. The batch of 244/PR8 that was examined had previously been shown to protect mice from disease caused by influenza B/Lee virus.

DI 244/PR8 influenza A virus (#813) was UV irradiated for 40 seconds to remove all infectivity. 244/PR8 is a concentrated purified virus preparation that has $2\times10^5$ HAU/ml and approximately $2\times10^{12}$ physical particles/ml. Influenza B/Lee/40 (#795) is allantoic fluid and was used at an arbitrary high dose of 1/0 dilution to ensure infection of all cells, and to give replication of the DI influenza A RNA every chance of succeeding. 244/PR8 was serially diluted (see Table 7 below) in 1/10 B/Lee that contained penicillin and streptomycin as a precaution against bacterial contamination of the eggs. 10-day old embryonated chicken's eggs (3 eggs/sample) were injected with 100 μl of the mixture and various controls (Table 7).

TABLE 7

Scheme for inoculation of embryonated chicken's eggs with mixtures of influenza A DI 244/PR8 and infectious influenza B

| | 244/PR8 | B/Lee* |
|---|---|---|
| A | 1/10 | + |
| B | 1/100 | + |
| C | 1/1000 | + |
| D | 1/10000 | + |
| E | None | + |
| F | 1/10 | None |
| G | None | None |

*a 1/10 dilution of #795

Eggs were incubated at 33° C. for 24 h, chilled and allantoic fluids harvested. Approximately 2 ml from each of 3 eggs was pooled and stored at −70° C. The amount of viral haemagglutinin (HA) in allantoic fluids was determined by endpoint titration and agglutination of added chicken red blood cells. RT-PCR was carried out using terminal primers to PR8 segment 1 RNA from which 244 RNA is derived.

Table 8 (row E) shows that B/Lee on its own grew well with a titre of $10^{3.5}$ HAU/ml.

244/PR8 on its own had no HA titre showing that it was entirely non-infectious. All mixtures of B/Lee and 244/PR8 (Table 8 rows A-D) gave approximately the same HA titre showing that 244/PR8 had not interfered with the multiplication of B/Lee.

TABLE 8

Production of haemagglutinin by eggs inoculated with mixtures of influenza A DI 244/PR8 and infectious influenza B*

| | 244/PR8 | B/Lee** | HAU/ml ($log_{10}$) |
|---|---|---|---|
| A | 1/10 | + | 3.1 |
| B | 1/100 | + | 3.7 |
| C | 1/1000 | + | 3.3 |
| D | 1/10000 | + | 3.25 |
| E | None | + | 3.5 |
| F | 1/10 | None | ≤1.6 |
| G | None | None | ≤1.6 |

*after incubation for 24 h at 33° C.
**a 1/10 dilution of #795
HAU, haemagglutinating units RNA was extracted from allantoic fluid and subjected to RT-PCR with terminal primers to PR8 RNA segment 1. FIG. 1 shows that eggs inoculated with 1/10 244/PR8 without B/Lee (Lane F) gave an amplicon of the size expected for 244 RNA and was presumably derived from residual inoculum RNA. This is not surprising as 244 RNA is known to persist in the lungs of intranasally inoculated mice for several weeks (unpublished data). The amplicon from the 1/10 244/PR8 mixed with B/Lee (Lane A) was no greater than that derived from the 244/PR8 on its own, showing that B/Lee had not replicated the 244/RNA. Lane B has a trace of 244 RNA in line with that expected from a 1/100 dilution. Note that Lane E that was inoculated with B/Lee alone contained an amplicon, presumably the result of non-specific priming; all other eggs inoculated with B/Lee have that amplicon, in confirmation of the presence of that virus.

A parallel experiment in which an attempt was made to replicate non-infectious 244 RNA using influenza A/mallard/England/7277/06 instead of B/Lee (data not shown) resulted in the increase in amount of all 244 RNA amplicons at dilutions of 1/10 to 1/10000 over that of the 244 RNA on its own. For this RT-PCR we used a junction-specific primer specific to 244 RNA to avoid confusion with any other endogenous segment 1 DI RNAs that might have been present or might have arisen de novo. This experiment served as a positive control.

In conclusion, the influenza B/Lee did not replicate the 244 RNA present in DI influenza A virus 244/PR8 under conditions designed to facilitate such an event.

There was thus no evidence of genetic interaction of influenza B/Lee with DI influenza A virus.

EXAMPLE 4

Comparison of PVM-Induced Clinical Disease in BALB/c and C3H/He-mg Mice in Order to Confirm the Suitability of C3H/He-mg Mice for PVM Experimentation In this and following examples, experiments were carried out to assess the effect of using DI influenza A virus containing influenza virus interfering RNA, on infection in mice caused by pneumonia virus of mice (PVM). Since all previous influenza A work had been carried out with C3H/He-mg mice, this was the preferred mouse strain to use. However it was first necessary to determine that PVM caused its typical disease pattern, as seen in BALB/c mice, in the C3H/He-mg mice.

Preparation of DI Influenza A Virus

Active DI virus was prepared by 40 second UV irradiation of a stock of DI influenza virus. Inactive DI virus was prepared by 8 minute UV irradiation of the same stock of influenza virus. Stocks were diluted as appropriate.

Treatment with DI Influenza A Virus

Mice were lightly anaesthetised using ether. DI virus was introduced by bilateral intranasal inoculation with a total of 40 μl of inoculum. Mice recovered very quickly and were observed to ensure that they did not show any adverse signs.

Infection with Pneumonia Virus of Mice (PVM)

All experiments used the same stock of PVM strain J3666. This has been shown to be highly pathogenic. Mice were first anaesthetised by intraperitoneal injection of a mixture of 9 mg/ml ketamine and 2 mg/ml xylazine in PBS. Animals were then inoculated with a total volume of 50 μl of virus (typically approximately 500 p.f.u. of virus unless indicated otherwise) by intranasal inoculation. All infections were carried out in a class I microbiological cabinet. Mice were allowed to recover and placed in an isolator.

Following the Process of Infection

Mice were monitored daily. All groups of mice were weighed and individual mice were scored for the presence of clinical signs of infection. Any mice showing the most severe clinical signs were killed in accordance with the requirements of the Home Office license under which the work was conducted. The description of clinical signs for PVM infection is shown in Table 9 below. The table identifies the symptoms of disease in mice infected with pathogenic strains of pneumonia virus of mice. In some strains the progression of disease is more rapid and some symptoms cannot be readily seen, e.g. cyanosis of ears and tail are readily seen in albino strains but not dark coloured strains of mice. The time between level 2 and 4 can be short and often levels 2 and 3 cannot be distinguished as completely separate.

TABLE 9

Description of clinical signs for PVM infection in mice.

| Score | Symptoms |
|---|---|
| 1 | Healthy, with no sign of illness |
| 2 | Ruffled fur, especially on back of neck |
| 3 | Piloerection. Possibly deeper breathing. Less alert |
| 4 | Obvious weight loss. Laboured breathing. Possible tremors |
| 5 | Abnormal gait and difficulty walking. Laboured breathing. Frequently emaciated. May show cyanosis of tails and/or ears |
| 6 | Dead |

The experiment of Example 4 was carried out in order to establish the effect of PVM infection on C3H/He-mg mice.

While the initial experiments describing the isolation of PVM used an outbred line all work published in the last 20 years have used inbred strains of mice. The pattern of disease was first published using BALB/c mice and subsequently the symptoms have been confirmed to be identical in C57/BL6 mice. No descriptions of PVM infection in C3H/He-mg mice have been published. For comparability with the influenza virus protection work which was carried out using C3H/He-mg mice these were tested for their response to PVM infection. BALB/c mice were used as a standard for comparison.

Five groups, each consisting of 4 mice, either BALB/c or C3H/He-mg mice were used. A stock of PVM strain J3666 was used at four dilutions, neat (approximately 5000 p.f.u. in 50 μl 1/3 (approximately 1700 p.f.u. in 50 μl), 1/10 (approximately 500 p.f.u. in 50 μl) and 1/30 (approximately 170 p.f.u. in 50 μl). Each group of four mice were inoculated with 50 μl of the appropriate dilution of virus and a control group was inoculated with 50 μl of sterile PBS as control. The groups of mice were weighed each day and were observed for clinical signs of infection.

Figure 2A:
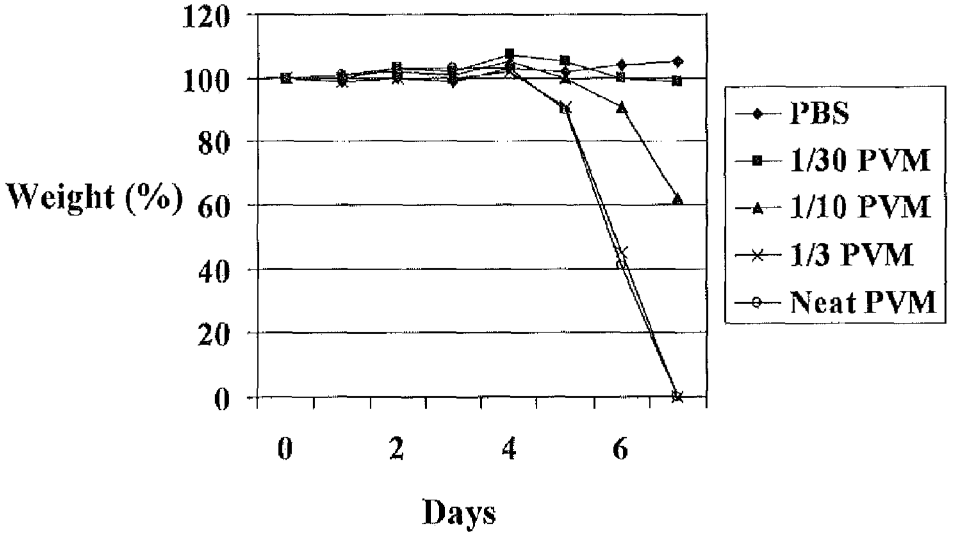
FIG. 2A is a plot of data showing the effect of different doses of PVM on C3H/He-mg mice (4 mice per group).
Figure 2B:
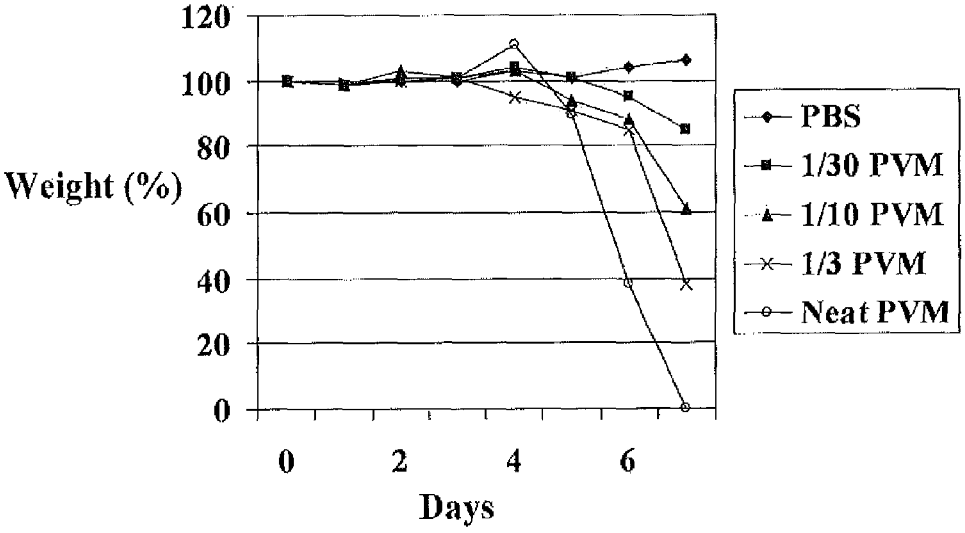
FIG. 2B is a plot of data showing the effect of different doses of PVM on BALB/c mice (4 mice per group).

The results are shown in FIG. 2A and FIG. 2B. In this and all subsequent PVM experiments the weights of the groups of animals are plotted with the initial weight taken as 100%. Every weight taken thereafter is presented as relative to the initial value. The weight of a dead mouse is taken as 0 g. Thus if a group began with 5 mice with a total weight of 100 g (all being 20 g) and one mice died but the other mice stayed the same weight, the weight of the group would be 80 g and hence 80% of the original. When all mice are dead the total weight is 0 g and hence 0% of the original. The effect of PVM infection in C3H/He-mg mice is the same as in BALB/c mice. All subsequent experiments with DI influenza A virus used C3H/He-mg mice.

EXAMPLE 5

Determination of the Protective Effect of DI Influenza A Virus 244/PR8 Against PVM Challenge-I This experiment sought to investigate the potential protective capacity of DI influenza A virus 244/PR8 against a PVM challenge in C3H/He-mg mice.

Example 4 confirmed that PVM infection in C3H/He-mg mice followed the same pattern of disease progression as established previously in BALB/c mice. In this experiment the highest dose of DI influenza A virus possible was used to have the highest probability of observing an effect. At these high levels the inactive DI influenza A virus had shown some efficacy against infectious influenza A virus.

DI influenza A virus stock 244/PR8 #812 (244/PR8) was prepared as described above. This was undiluted material i.e. 12 μg/mouse and 10-fold more than in 'standard' tests with an influenza A virus challenge. Mice were administered either active DI influenza A virus or inactive DI influenza A virus using the standard procedure described above. Mice were then challenged with PVM 24 hours later. PVM strain J3666 was used at 1/3 dilution (approximately 1700 p.f.u. in 50 μl).

Figure 3:
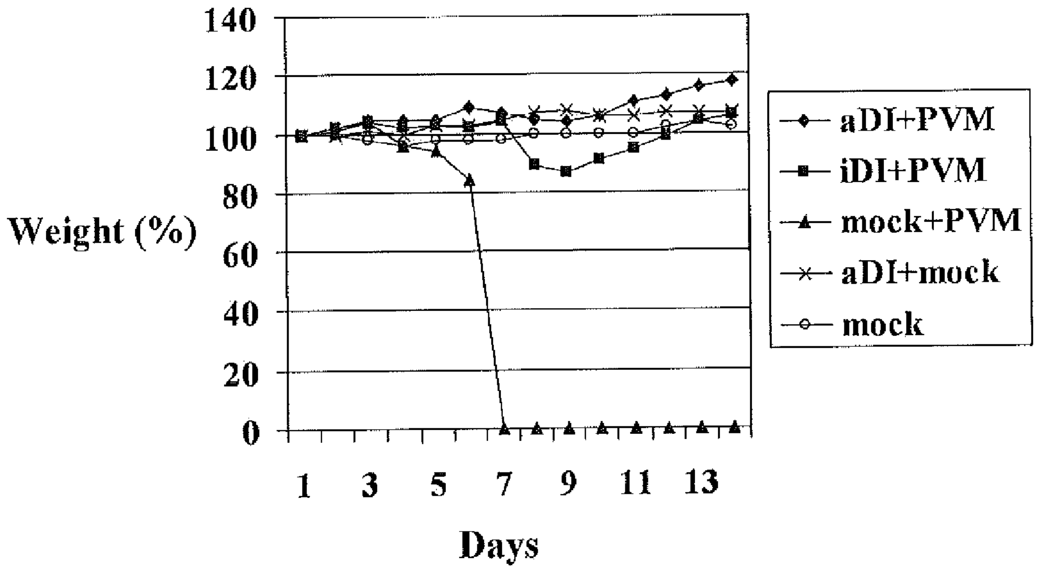
FIG. 3 is a plot of data showing the protective effect of undiluted DI influenza A virus against PVM challenge in C3H/He-mg mice.

Treatments were:

1. active DI influenza A virus+PVM−5 mice
2. inactive DI influenza A virus+PVM−5 mice
3. mock inoculation+PVM (i.e. no DI influenza A virus in initial inoculation)−4 mice
4. active DI influenza A virus and no challenge (i.e. DI influenza A virus+mock)−2 mice
5. mock inoculation, no challenge (i.e. no DI influenza A virus in the initial inoculation)−3 mice The weights of the groups of animals were plotted with the weight one day after PVM infection taken as 100%, as shown in FIG. 3.

Control (mock+PVM) shows that the PVM was fully infectious. Treatment with active DI influenza A virus eliminated signs of infection with PVM, though there was a small decline in the weight of this group at days 7-10. Mice treated with inactive DI influenza A virus and subsequently challenged with PVM showed modest clinical signs at days 8 and 9 and significant weight loss from day 8 onwards, though there was weight gain towards the end of the experiment. The remaining two control groups behaved as expected.

The observation of protection against PVM challenge was surprising. The less effective protection with inactive DI influenza A virus suggested that, either there was a non-specific effect due to the 'load' of virus particles used in the inoculum or that the high concentration of DI influenza A virus used was conferring protection by a non-specific route.

EXAMPLE 6

Determination of the Protective Effect of DI Influenza A Virus 244/PR8 Against PVM Challenge-II Example 5 suggested that DI influenza A virus may be able to confer protection against challenge with PVM but that this may be non-specific. The data from that experiment was obtained using a DI influenza A virus inoculum 10-fold higher than used in influenza virus challenge experiments. To make a more appropriate comparison, the experiment was repeated using the standard level of DI influenza A virus inoculum (1.2 μg/mouse). This experiment therefore repeats Example 5, but uses a 10-fold lower dose of DI influenza A virus.

Mice were inoculated with DI influenza A virus 244/PR8 prepared and delivered using the standard technique described above. After 24 hours mice were challenged with PVM strain J3666 used at 1/5 dilution (approximately 1000 p.f.u. in 50 μl).

Figure 4:
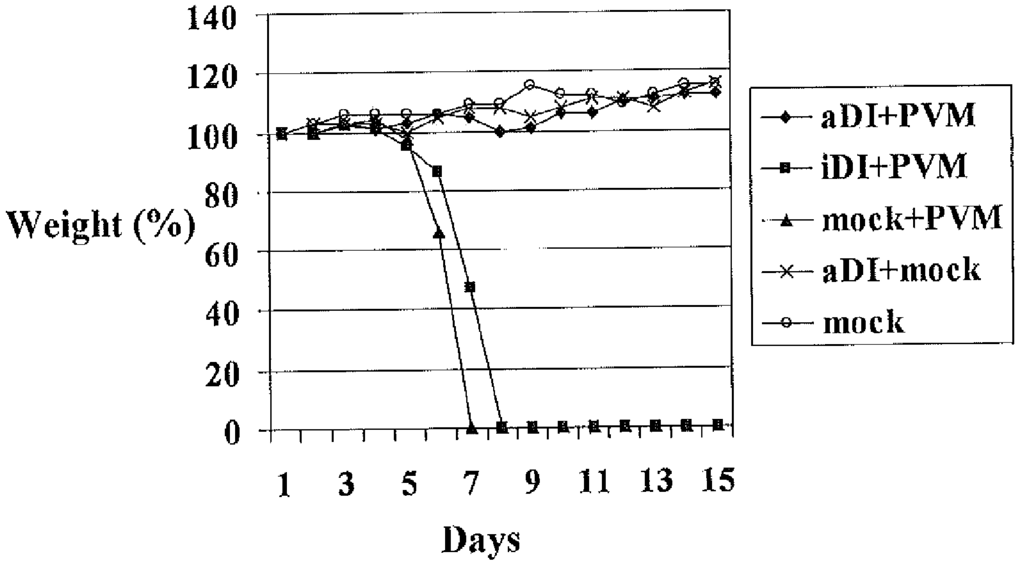
FIG. 4 is a plot of data showing the protective effect of diluted DI influenza A virus against PVM challenge in C3H/He-mg mice.

The experimental groups were:

1. active DI influenza A virus+PVM–5 mice
2. inactive DI influenza A virus+PVM–5 mice
3. mock inoculation+PVM (i.e. no DI influenza A virus in initial inoculation)–4 mice
4. active DI influenza A virus and no challenge (i.e. DI influenza A virus+mock)–2 mice
5. mock inoculation, no challenge (i.e. no DI influenza A virus in the initial inoculation)–2 mice FIG. 4 shows the weights of the groups of animals plotted with the weight one day after PVM infection taken as 100%. Active DI influenza A virus conferred complete protection against the presentation of clinical signs following PVM infection in all animals. There was a small reduction in weight on days 8 and 9 of this group. The inactive DI influenza A virus showed no protection with all mice succumbing to infection, though there may have been a very small delay in the progression of disease in this group when compared to the control which received no DI influenza A virus inoculation.

These data show very clear protection associated with inoculation with active DI influenza A virus and none with inactive DI influenza A virus. Taken together with the data from Example 5, when a 10-fold higher dose of DI influenza A virus was used, this suggests that DI influenza A virus may have the capacity to act through another system. This would suggest that at high concentration influenza virus particles may be able to induce another system of antiviral defense, but that at lower doses this capacity is higher in active DI influenza A virus preparations than in inactivated preparations.

EXAMPLE 7

Investigation of the Duration of Protection Exerted by DI Influenza A Virus 244/PR8 Against PVM Infection The protection conferred against PVM infection by DI influenza A virus may be due to one or more factors. This experiment was conducted to investigate the duration of protection against PVM infection conferred by DI influenza A virus.

Animals were treated with DI influenza A virus 244/PR8 (active or inactive) according to the standard procedure described above in Example 6. All animals were observed for 6 days and then challenged with PVM strain J3666 at 1/5 dilution (approximately 1000 p.f.u. in 50 μl). Animals were observed and each group weighed daily.

Figure 5:
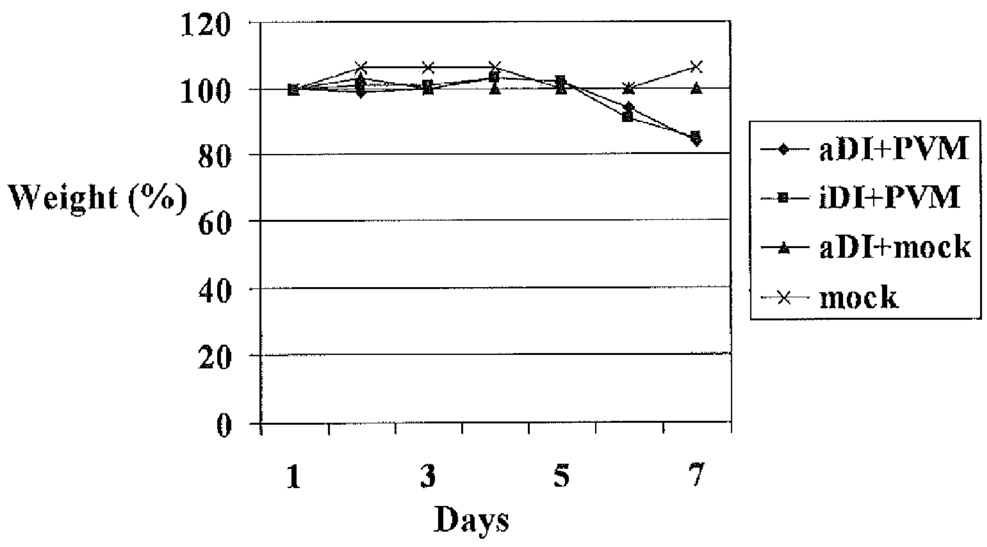
FIG. 5 is a plot of data showing the longevity of DI influenza A virus-mediated protection against PVM challenge in C3H/He-mg mice. Mice were challenged 6 days after treatment with DI influenza A virus.

The experimental groups were:

1. active DI influenza A virus+PVM–5 mice
2. inactive DI influenza A virus+PVM–5 mice
3. active DI influenza A virus and no challenge (i.e. DI influenza A virus+mock)–2 mice
4. mock inoculation, no challenge (i.e. no DI influenza A virus in the initial inoculation)–1 mouse FIG. 5 shows a plot of the time course of the weights of the groups of animals. The weight of animals one day after PVM infection is taken as 100%. All mice challenged with PVM succumbed to the infection and were culled at day 7 in accordance with the requirements of the Home Office license under which the work was performed.

The protection afforded by the active DI influenza A virus was lost by day 7 after inoculation. This would be in agreement with the possibility of DI influenza A virus generating a short-lived interferon response.

EXAMPLE 8

Determination of the Relationship Between Dose of DI Influenza A Virus 244/PR8 and Protection Against PVM Infection Examples 5 and 6 suggest there may also be a dose-related response for protection conferred against PVM infections. This experiment sought to determine the level of DI influenza A virus necessary to provide protection against challenge with PVM. Three different levels of DI influenza A virus were used.

Stocks of DI influenza A virus (244/PR8) were prepared and administered to mice. 24 hours after treatment mice were challenged with PVM strain J3666 at 1/5 dilution (approximately 1000 p.f.u. in 50 μl). Animals were observed and each group weighed daily.

The experimental groups were:

1. 1/10 dilution of active DI influenza A virus (1.2 ng/mouse)+PVM challenge (NB this is the 'standard' dose of DI influenza A virus used in previous experiments)–5 mice.
2. 1/100 dilution of active DI influenza A virus (120 ng/mouse)+PVM challenge–5 mice.
3. 1/1000 dilution of active DI influenza A virus (12 ng/mouse)+PVM challenge–5 mice.
4. 1/10 dilution of inactive DI influenza A virus (1.2 μg/mouse)+PVM challenge–5 mice.
5. 1/10 dilution of active DI influenza A virus (1.2 μg/mouse), no challenge–2 mice.
6. Mock inoculated, no challenge–2 mice.

Figure 6:
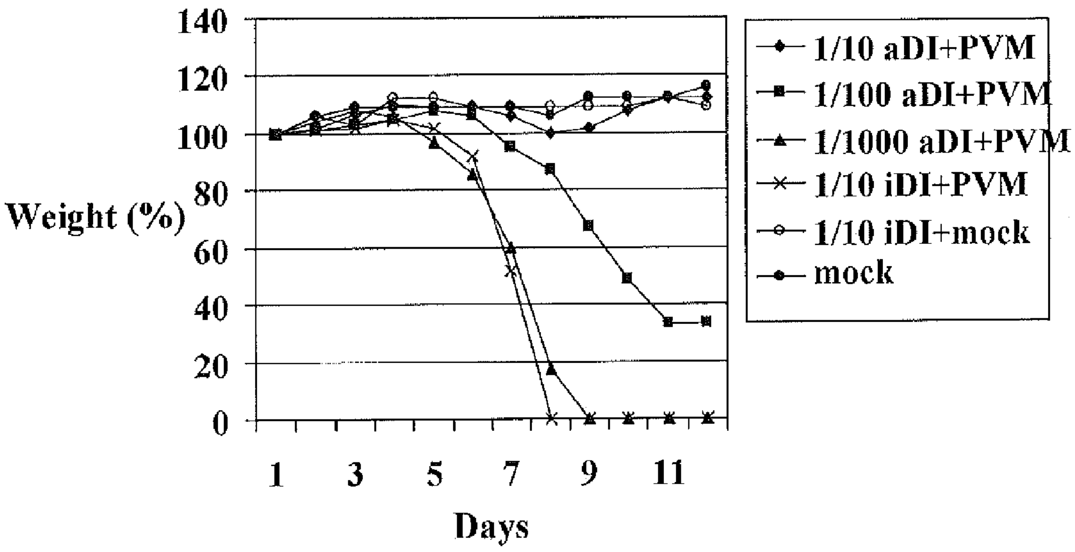
FIG. 6 is a plot of data showing the level of DI influenza A virus at which protection is afforded against PVM challenge in C3H/He-mg mice.

FIG. 6 shows the weights of the groups of animals plotted over time with the weight one day after PVM infection taken as 100%. The data show a clear dose-dependent response with clear protection at 1/10 dilution (as seen in other experiments) a partial protection with 1/100 dilution and essentially no protection at 1/1000 dilution. Notable is the slight drop in weight of the mice treated with 1/10 dilution which is exactly as seen in previous experiments despite no overt external symptoms being present.

EXAMPLE 9

Evaluation of the Reproducibility of Protection Exerted by DI Influenza A Virus 244/PR8 Against PVM Infection This experiment seeks to repeat Example 8 and demonstrate reproducibility.

Figure 7:
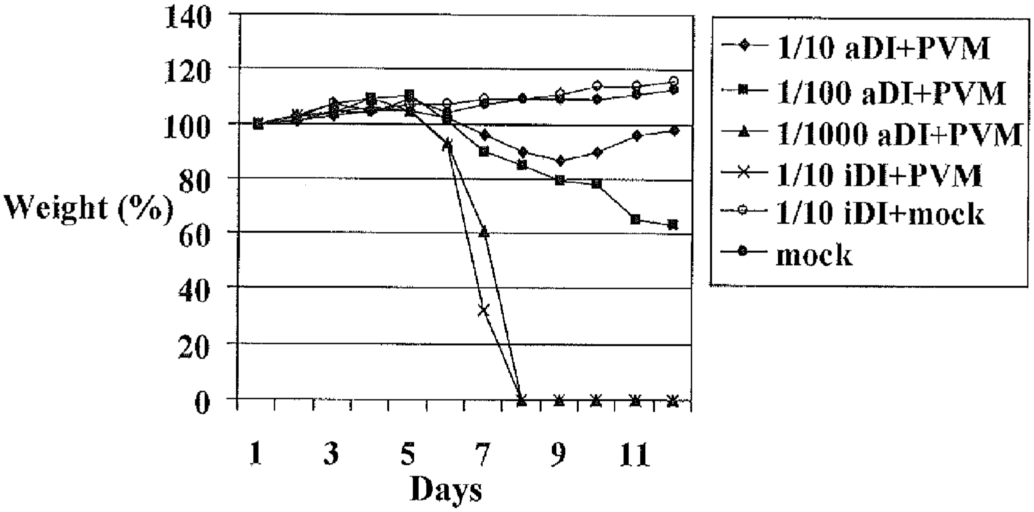
FIG. 7 is a plot of further data from another experiment showing the level of DI influenza A virus at which protection is afforded against PVM challenge in C3H/He-mg mice.

FIG. 7 shows the weights of the groups of animals were plotted over time with the weight one day after PVM infection taken as 100%. A dose-response is clear. In this experiment the 1/10 dilution did not protect as completely as previously and there were some minor clinical signs of infection associated with the decline in weight. The clinical signs were restricted to a single mouse on each of days 8, 10 and 12. Here the 1/100 dilution of DI influenza A virus showed a fair degree of protection but the 1/1000 dilution was not effective.

EXAMPLE 10

Determination of the Duration of Protection Against PVM Infection Afforded by DI Influenza A Virus 244/PR8

This experiment seeks to further define the duration of protection against PVM infection afforded by DI influenza A virus (see EXAMPLE 7).

The DI influenza A virus 244/PR8 stock #813 was used and diluted 1/10 (1.2 μg/mouse).

Figure 8:
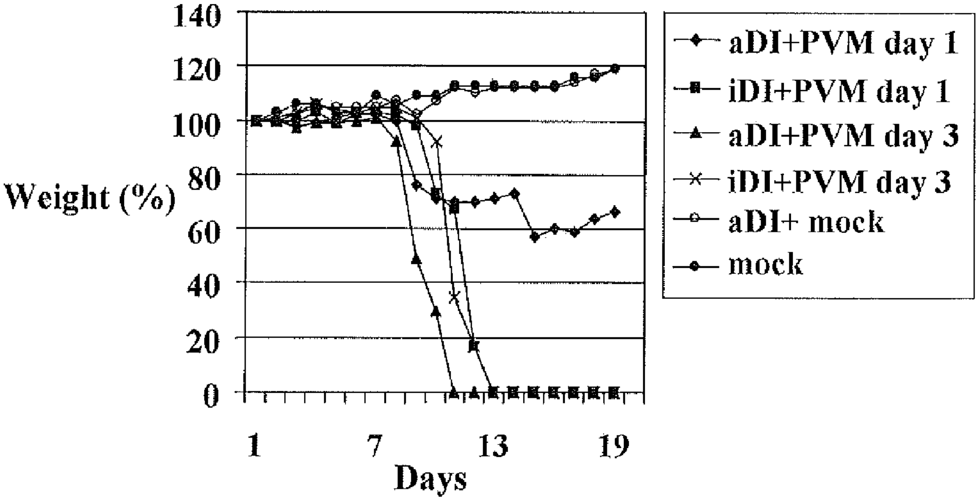
FIG. 8 is a plot of further data from another experiment showing the duration of protection afforded. Mice were challenged with PVM at 1 or 3 days after treatment with DI influenza A virus, as indicated.

The experimental groups consisted of:

1. Active DI influenza A virus+PVM one day post treatment−5 mice
2. Inactive DI influenza A virus+PVM one day post treatment−5 mice
3. Active DI influenza A virus+PVM three days post treatment−5 mice
4. Inactive DI influenza A virus+PVM three days post treatment−5 mice
5. Active DI influenza A virus and no challenge (i.e. DI influenza A virus+mock)−2 mice
6. Mock inoculation, no challenge (i.e. no DI influenza A virus in the initial inoculation)−2 mice FIG. 8 shows the weights of the groups of animals plotted over time with the weight on the day of DI influenza A virus treatment taken as 100%. The protection with active DI influenza A virus when challenged at day 1 post treatment was not as strong as seen previously. This is likely to be due to the dose level being sub-optimal.

Despite this, it can clearly be seen that the protective effect is lost by day 3 post treatment.

EXAMPLE 11

Determination of the Therapeutic Activity of DI Influenza A Virus 244/PR8 Against PVM Infection DI influenza A virus has been shown to have both prophylactic and therapeutic activity in influenza A virus infections. An assessment of the therapeutic capacity in PVM infections may give some insight into the mechanism of action of the DI influenza A virus and also its potential value for treatment of ongoing pneumovirus infections.

DI influenza A virus 244/PR8 stocks (1.2 μg/mouse) were prepared as described above. For those mice receiving DI influenza A virus treatment was conducted as a first procedure. Subsequent inoculations were then performed. Mice were challenged with PVM strain J3666 at 1/5 dilution (approximately 1000 p.f.u. in 50 μl). Animals were observed and each group weighed daily.

Figure 9:
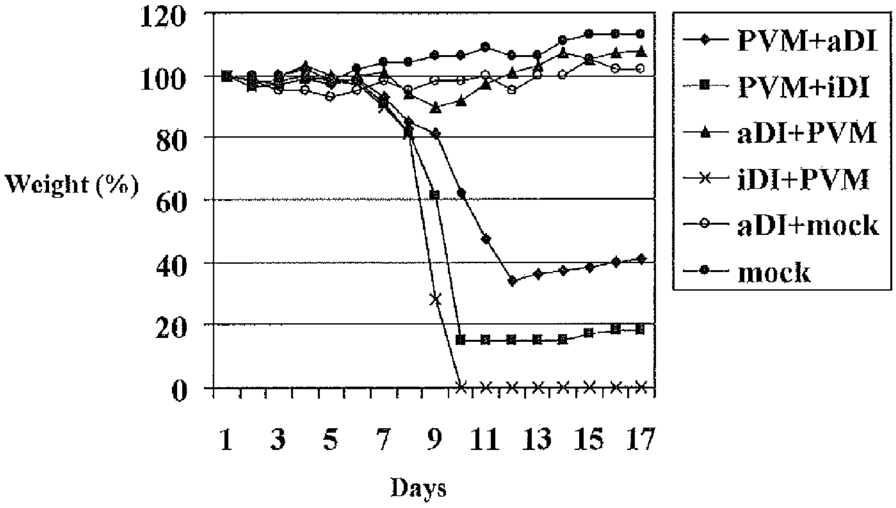
FIG. 9 is a plot of data showing how the weights of groups of mice changes over time in response to treatment with DI influenza A virus before or after PVM challenge.

The experimental groups were:

1. PVM infection followed by active DI influenza A virus one day post infection−5 mice
2. PVM infection followed by inactive DI influenza A virus one day post infection−5 mice
3. Active DI influenza A virus+PVM one day post treatment−5 mice
4. Inactive DI influenza A virus+PVM one day post treatment−5 mice
5. Active DI influenza A virus and no challenge (i.e. DI influenza A virus+mock)−2 mice
6. Mock inoculation, no challenge−2 mice FIG. 9 shows the weights of the groups of animals plotted over time with the weight on the day of first treatment (inoculation with DI influenza A virus or infection with PVM) taken as 100%. The data confirm protection from infection when using active DI influenza A virus inoculated 24 hours prior to PVM infection. As before, there is a small reduction in weight of the group which in this case was associated with the appearance of the mildest symptoms in one mouse, with no symptoms in the others.

As before, treatment with inactive DI influenza A virus provided no protection. Treatment with active DI influenza A virus 24 hours after infection with PVM did not confer complete protection but did ameliorate the disease when compared to controls. Surprisingly, treatment with inactive DI influenza A virus showed a marginal effect (one surviving mouse which had previously shown symptoms of disease). The data are evidence for a degree of therapeutic efficacy under the conditions used.

EXAMPLE 12

Demonstration that Type I Interferon is Found in the Lung but Not in the Serum of Mice Inoculated Intranasally with DI Influenza A Virus 244/PR8

C3H/He-mg mice (16-20 g and approximately 5 weeks of age) were inoculated intranasally under light anaesthesia with DI influenza A virus 244/PR8 (#812) or UV-inactivated (i) DI influenza A virus or with diluent—using the procedure described above for protection experiments. In separate experiments mice were inoculated with 12 or 1.2 μg of DI virus per mouse. Two mice per group were used. The DI virus is not infectious and no other infectious virus is used. Mice were killed and lungs removed at 1 day after inoculation and frozen at −70° C. Blood was also taken from the heart, and processed for serum which was stored in the same way. Lungs from each mouse were stored separately. Sera from both mice were pooled.

A bioassay used mouse L cells and Semliki Forest virus (SFV) whose multiplication is sensitive to interferon in a 96-well plastic plate. Interferon inhibits the cytopathology caused by SFV. The minimum dose of SFV that would reliably kill cells in 5-6 days was determined empirically.

Lungs from one mouse were thawed and ground with sand, with a pestle and mortar, in 1 ml PBS containing 0.1% bovine serum albumen. After low-speed centrifugation to remove sand and debris, the supernatant was aliquotted and refrozen preparatory for interferon assay. Because lung extracts were toxic for cells the assay commenced at a 1/5 dilution, but some toxicity was still observed at this dilution. Results from toxic samples were ignored. Sera were less toxic, but as there was less material available dilutions usually started at 1/5.

For the assay, interferon (lung supernatant or serum) was serially diluted and added to cells 1 day before the cells were infected to allow time for induction of the antiviral state. Medium was removed next day and replaced with SFV and incubated for 5-6 days. Remaining cells were then stained with the vital dye neutral red. The dye then extracted under alkaline conditions which enhance the colour, and quantitated using an ELISA reader.

In addition, each plate contained a virus control, cell control and a positive interferon control—a commercially sourced recombinant mouse beta interferon (PBL Biomedical Laboratories).

Figure 10:
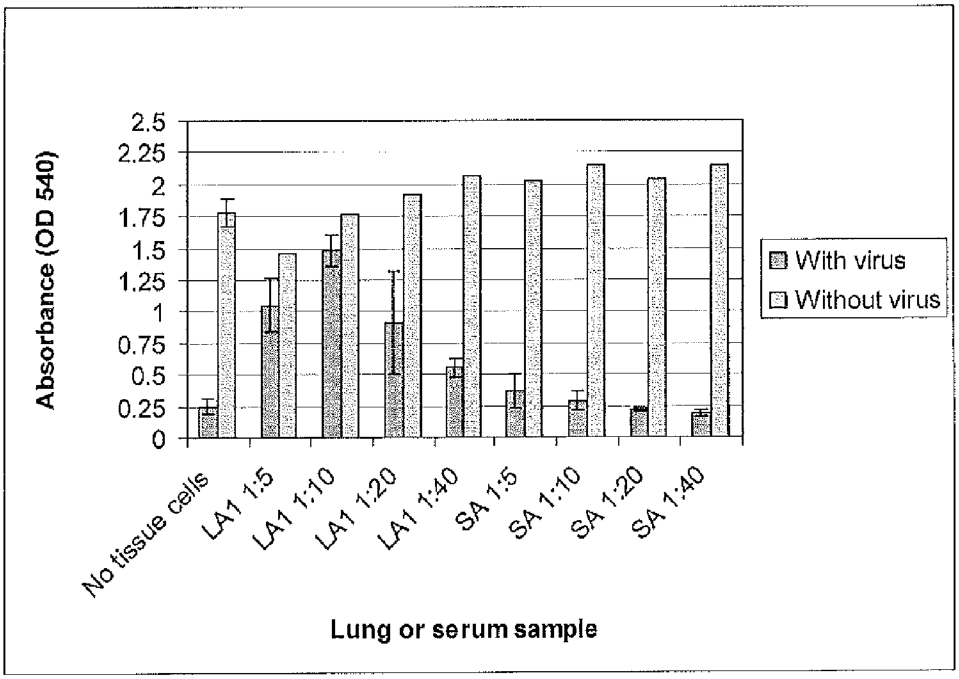
FIG. 10 shows the results of an assay for interferon carried out on the lung (L) and serum (S) samples at 1 day after intranasal inoculation of mice with neat DI influenza A virus. The OD of neutral red stained cells was read at 6 days after infection. 'Virus' refers to the presence of Semliki Forest virus in the assay.
Figure 11:
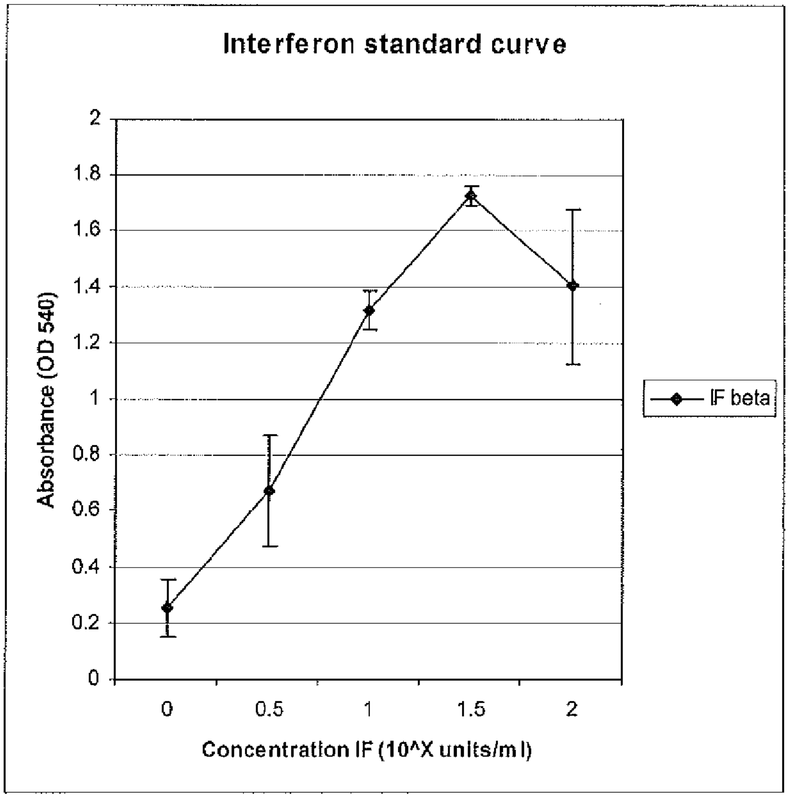
FIG. 11 shows a titration curve of control beta interferon on the same microtiter plate used for FIG. 10 and Table 10.

FIG. 10 and Table 10 show that the lungs of mice inoculated with neat DI influenza A virus 244/PR8 were positive for interferon up to a 1/40 dilution. Some toxicity is seen with the most concentrated (1/5) lung sample, but the 1/10 dilution protected 84.4% of cells, 6-fold more surviving cells than in the virus control with no added interferon. In contrast serum from the same mouse showed no evidence of interferon activity. In mice inoculated with 1/10 DI influenza A virus no interferon was detected with a 1/10 dilution of lung extract or with 1/5 serum (Table 11). Titration of the beta interferon standard from the plate used for FIG. 10/Table 10 is shown in FIG. 11.

TABLE 10

Assay for interferon in lung and serum at 1 day after inoculation of mice with neat DI influenza A virus

| Mouse inoculum | Lungs/serum Dilution assayed | Lungs | | Serum | |
|---|---|---|---|---|---|
| | | OD with virus: OD with no virus (%) | Relative inhibition of c.p.e* | OD with virus: OD with no virus (%) | Relative inhibition of c.p.e* |
| DI 1/1 | 1/5 | Toxic | Na | 18.3 | 1.3 |
| | 1/10 | 84.4 | 6.0 | 13.5 | 1.0 |
| | 1/20 | 47.4 | 3.4 | 10.8 | 0.8 |
| | 1/40 | 26.6 | 1.9 | 8.8 | 0.6 |
| None | Na | | 14.2 | 1.0 | 1.0 |

DI, DI influenza A virus
*Relative inhibition of c.p.e, OD virus: OD no virus (%) for wells with added putative interferon/OD
virus: OD no virus for wells with no added interferon from column 3.
Na, not applicable.
Toxic, 18.5% toxicity with this lung sample

TABLE 11

Assay for interferon in lung and serum at 1 day after inoculation of mice with 1/10 DI influenza A virus

| Mouse inoculum | Lungs/serum Dilution assayed | Lungs | | Serum | |
|---|---|---|---|---|---|
| | | OD with virus: OD with no virus (%) | Relative inhibition of c.p.e* | OD with virus: OD with no virus (%) | Relative inhibition of c.p.e* |
| DI 1/10 | 1/5 | Toxic | Na | 13.0 | 0.6 |
| | 1/10 | 20.9 | 0.9 | 10.0 | 0.4 |
| | 1/20 | 18.9 | 0.8 | 11.6 | 0.5 |
| | 1/40 | 15.2 | 0.7 | 11.2 | 0.5 |
| None | Na | | 22.4 | 1.0 | 1.0 |

DI, DI influenza A virus
*Relative inhibition of c.p.e, OD virus: OD no virus (%) for wells with added putative interferon/OD
virus: OD no virus for wells with no added interferon from column 3.
Na, not applicable.
Toxic, 46% toxicity with this lung sample Inactivated DI influenza A virus did not stimulate interferon at a lung dilution of 1/10 or a serum dilution of 1/5 (see Tables 12 & 13 below).

TABLE 12

Assay for interferon in lung and serum at 1 day after inoculation of mice with neat inactivated DI influenza A virus

| Mouse inoculum | Lungs/serum Dilution assayed | Lungs | | Serum | |
|---|---|---|---|---|---|
| | | OD with virus: OD with no virus (%) | Relative inhibition of c.p.e* | OD with virus: OD with no virus (%) | Relative inhibition of c.p.e* |
| iDI 1/1 | 1/5 | Toxic | Na | 13.3 | 0.5 |
| | 1/10 | 37.5 | 1.4 | 16.2 | 0.6 |
| | 1/20 | 22.1 | 0.8 | 15.8 | 0.6 |

TABLE 12-continued

Assay for interferon in lung and serum at 1 day after inoculation of mice with neat inactivated DI influenza A virus

| Mouse inoculum | Lungs/serum Dilution assayed | Lungs | | Serum | |
|---|---|---|---|---|---|
| | | OD with virus: OD with no virus (%) | Relative inhibition of c.p.e* | OD with virus: OD with no virus (%) | Relative inhibition of c.p.e* |
| | 1/40 | 16.4 | 0.6 | 18.3 | 0.7 |
| None | Na | | 27.2 | 1.0 | 1.0 |

iDI, inactivated DI influenza A virus
*Relative inhibition of c.p.e, OD virus: OD no virus (%) for wells with added putative interferon/OD
virus: OD no virus for wells with no added interferon from column 3.
Na, not applicable.
Toxic, 65% toxicity with this lung sample

TABLE 13

Assay for interferon in lung and serum at 1 day after inoculation of mice with neat inactivated DI influenza A virus from a second mouse

| Mouse inoculum | Lungs/serum Dilution assayed | Lungs | | Serum | |
|---|---|---|---|---|---|
| | | OD with virus: OD with no virus (%) | Relative inhibition of c.p.e* | OD with virus: OD with no virus (%) | Relative inhibition of c.p.e* |
| iDI 1/1 | 1/5 | Toxic | Na | Not done | |
| | 1/10 | Toxic | Na | | |
| | 1/20 | 11.4 | 1.15 | | |
| | 1/40 | 9.6 | 1.0 | | |
| None | Na | | 9.9 | 1.0 | |

iDI, inactivated DI influenza A virus
*Relative inhibition of c.p.e, OD virus: OD no virus (%) for wells with added putative interferon/OD
virus: OD no virus for wells with no added interferon from column 3.
Na, not applicable.
Toxic, 34% toxicity with the 1/5 and 1/10 lung samples Putative interferon (strictly an unidentified soluble, virus-inhibiting entity) was detected in the lungs of mice after intranasal inoculation of neat DI influenza A virus, but not in the serum of the same mouse. Approximately 50% inhibition was seen at a 1/20 dilution of lung extract. No interferon was identified in lungs or serum from mice inoculated with 1/10 DI influenza A virus, or with neat UV-inactivated DI influenza A virus.

EXAMPLE 13

Demonstration that Type I Interferon Induced in Mice Inoculated Intranasally with DI Influenza A Virus 244/PR8 can be Detected in the Lungs for 2 Days C3H/He-mg mice were inoculated with neat DI virus influenza A virus (12 μg/mouse) as described for EXAMPLE 12 except that lungs removed at 1, 2 and 4 days after inoculation.

The interferon bioassay used was as described for EXAMPLE 12.

Table 14 shows strong antiviral activity in lung extracts taken on days 1 and 2, but not on day 4 (≤1/10). The 50% endpoint on day 1 was ≥1/40, and on day 2 was approximately 1/30. No interferon was present in serum (1/5) taken on day 2 (data not shown).

TABLE 14

Assay for interferon in mouse lungs at days 1, 2 and 4 after intranasal inoculation with neat DI influenza A virus

| | | Day 1 | | Day 2 | | Day 4 | |
|---|---|---|---|---|---|---|---|
| Mouse inoculum | Dilution assayed | OD with virus: OD with no virus (%) | Interferon present | OD with virus: OD with no virus (%) | Interferon present | OD with virus: OD with no virus (%) | Interferon present |
| DI 1/1 | 1/5 | Toxic | | Toxic | | Toxic | |
| | 1/10 | 72.8 | + | 91.9 | + | 8.1 | − |
| | 1/20 | 85.6 | + | 80.4 | + | 9.4 | − |
| | 1/40 | 85.2 | + | 20.1 | ± | 9.8 | − |
| None | Na | 7.2 | Na | 7.2 | Na | 8.8 | Na |

DI, DI influenza A virus
Toxic, some toxicity
Na, not applicable

Interferon was present in lungs at 1 and 2 days after inoculation, but was not detected 4 days after inoculation, suggesting that the induced interferon has a relatively short half-life in that location. Note that this experiment does not address the question of the duration of the interferon-induced anti-viral state in the lungs

EXAMPLE 14

Demonstration that Type I Interferon is not Induced in the Lungs or Serum of Mice Inoculated Intranasally with DI Influenza A Viruses 220/Vic or 220/PR8

C3H/He-mg mice were used as described for EXAMPLE 12 except that neat (12 μg/mouse) 220/PR8 (#794) or 220/Vic (#798) DI or UV-inactivated (i) DI virus were inoculated.

The interferon bioassay used was as described for EXAMPLE 12.

Figure 12:
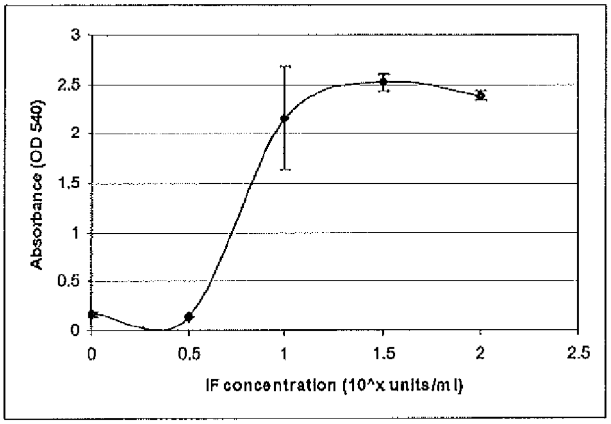
FIG. 12 shows a standard curve for measurements of control beta interferon on the same microtiter plate giving rise to values in Table 15.

No interferon was detected in the lungs or serum of mice inoculated with neat DI influenza A viruses 220/PR8 or 220/Vic or inactivated DI influenza A viruses 220/PR8 or 220/Vic (Tables 15, 16). There were no technical problems with the assay and each microtiter plate contained a standard titration of beta interferon to ensure that the assay was competent—an example is shown in FIG. 12. There were 2 mice per group and interferon was detected in neither of them.

TABLE 15

Failure to detect interferon in lungs or serum of mice after intranasal inoculation with neat DI influenza A virus 220/PR8 - samples taken at 1 day later

| | | DI | | iDI | |
|---|---|---|---|---|---|
| Mouse inoculum | Dilution assayed | Lungs OD with virus: OD with no virus (%) | Serum OD with virus: OD with no virus (%) | Lungs OD with virus: OD with no virus (%) | Serum OD with virus: OD with no virus (%) |
| DI 1/1 | 1/5 | 8.0 | Nd | Toxic | Nd |
| | 1/10 | 5.7 | 9.2 | 9.6 | 7.7 |
| | 1/20 | 5.3 | 7.9 | 5.4 | 7.2 |
| | 1/40 | 5.3 | 8.1 | 5.8 | 6.3 |
| None | Na | 9.7 | | 8.0 | |

DI, DI influenza A virus
Toxic, some toxicity
Na, not applicable

TABLE 16

Failure to detect interferon in lungs or serum of mice after intranasal inoculation with neat DI influenza A virus 220/Vic - samples taken at 1 day later.

| | | DI | | iDI | |
|---|---|---|---|---|---|
| Mouse inoculum | Dilution assayed | Lungs OD with virus: OD with no virus (%) | Serum OD with virus: OD with no virus (%) | Lungs OD with virus: OD with no virus (%) | Serum OD with virus: OD with no virus (%) |
| DI 1/1 | 1/5 | Toxic | Nd | 13.1 | Nd |
| | 1/10 | 8.1 | 6.4 | 6.1 | 7.3 |
| | 1/20 | 7.5 | 6.8 | 7.1 | 7.0 |
| | 1/40 | 7.9 | 6.6 | 5.6 | 6.5 |
| None | Na | 7.8 | | 8.0 | |

DI, DI influenza A virus
Toxic, some toxicity
Na, not applicable

DI influenza A viruses 220/PR8 or 220/Vic inoculated intranasally did not stimulate any detectable interferon in mouse lungs or serum. This contrasts with induction of interferon in cells engineered to express luciferase under the control of an interferon promoter, where 220/Vic stimulated interferon at 1/00 dilution and possibly 1/1000 dilution but neat 220/PR8 stimulated no interferon (EXAMPLE 17).

EXAMPLE 15

Demonstration that Type I Interferon is Found in the Serum but Not in the Lungs of Mice Injected Intraperitoneally with DI Influenza A Virus 244/PR8

C3H/He-mg mice were used as described for EXAMPLE 12 except that mice were injected intraperitoneally with 244/PR8 (#812) DI or UV-inactivated (i) DI virus, or with diluent. Each mouse received 20 μl of DI/iDI made up to 100 μl i.e. the same dose as given intranasally (12 μg/mouse). Two mice per group were used.

The interferon bioassay used was as described for EXAMPLE 12.

Table 17 shows that interferon was reproducibly detected in the serum of both mice injected intraperitoneally with DI influenza A virus at 1 day after inoculation. A dilution of approximately 1/120 protected about 50% of the cell monolayer. Little interferon was detected with iDI virus except possibly at 1/10 dilution of serum—14.5% and 44.4% inhibition in replicate mice (see Table 18). The highest concentration of lung extract (1/10) inhibited virus by around 3-fold in one mouse—the other extract was cytotoxic at that concentration.

TABLE 17

After intraperitoneal injection of mice with neat DI influenza A virus 244/PR8 a strong interferon response was found in serum but not lungs - samples were taken at 1 day after injection.

| | | Mouse 1 | | Mouse 2 | |
|---|---|---|---|---|---|
| Mouse inoculum | Dilution assayed | Lungs OD with virus: OD with no virus (%) | Serum OD with virus: OD with no virus (%) | Lungs OD with virus: OD with no virus (%) | Serum OD with virus: OD with no virus (%) |
| DI 1/1 | 1/10 | 21.4 | 91.8 | toxic | Na |
| | 1/20 | 5.8 | 89.3 | 7.1 | 95.1 |
| | 1/40 | 6.1 | 80.6 | 6.8 | 95.9 |
| | 1/80 | Nd | 85.2 | Nd | 66.6 |
| | 1/160 | Nd | 18.1 | Nd | 27.7 |
| None | Na | 7.2 | Na | 8.1 | Na |

DI, DI influenza A virus
Toxic, some toxicity
Na, not applicable;
Nd, not done

TABLE 18

After intraperitoneal injection of mice with neat iDI virus 244/PR8 no interferon was found in serum or lungs - samples taken as above.

| | | Mouse #1 | | Mouse #2 | |
|---|---|---|---|---|---|
| Mouse inoculum | Dilution assayed | Lungs OD with virus: OD with no virus (%) | Serum OD with virus: OD with no virus (%) | Lungs OD with virus: OD with no virus (%) | Serum OD with virus: OD with no virus (%) |
| DI 1/1 | 1/10 | 10.4 | 14.5 | 9.4 | 44.4 |
| | 1/20 | 8.4 | 8.1 | 6.8 | 8.5 |
| | 1/40 | 6.4 | 7.3 | 7.4 | 11.2 |
| | 1/80 | Nd | 7.8 | Nd | 10.3 |
| | 1/160 | Nd | 7.4 | Nd | 10.2 |
| None | Na | 9.8 | Na | 13.8 | Na |

DI, DI influenza A virus
Toxic, some toxicity
Na, not applicable;
Nd, not done

244/PR8 injected intraperitoneally into mice stimulated a strong interferon response in serum. The interferon assay gave significant inhibition of virus at 1/160, with 50% inhibition at approximately 1/120 dilution of serum. There was little if any interferon in the lungs—one mouse showed a slight virus inhibitory effect at a 1/10 dilution. This contrasts with intranasal inoculation of DI virus where interferon was stimulated in the lungs but not the serum. There appears to be more interferon stimulated by intraperitoneal than by intranasal inoculation of DI virus—respective day 1 50% titres were approximately 1/120 and 1/20. There is an inherent dilution factor in the preparation of the lung extract of approximately 2- to 3-fold, but this does not account for the difference in interferon stimulated.

EXAMPLE 16

Formal Identification that the Virus-Inhibitory Activity Appearing in Serum after Intraperitoneal Injection of Mice with of DI Influenza A Virus 244/PR8 is Type I Interferon All type I interferons (13 types of interferon-alpha and 1 interferon-beta protein) use the same receptor, which is a transmembrane protein with the interferon-binding region(s) in its external domain. Thus activity by any of them can be blocked by antibody to the external domain of the interferon type I receptor. Such an antibody, obtained from R&D Systems Inc. (lot number WXB01), was produced in goats by immunization with recombinant mouse interferon type I α/β receptor extracellular domain. IgG was purified by using a solid phase mouse interferon type I α/β receptor and affinity chromatography. The interferon source was the serum interferon induced in Experiment 4 by intraperitoneal injection of DI influenza A virus 244/PR8.

The standard interferon bioassay described above used mouse L cells and Semliki Forest virus (SFV) in a 96-well plastic plate. The minimum dose of SFV that would reliably detach cells from the plastic substrate in 5-6 days was determined empirically. Interferon inhibits the cytopathology caused by SFV.

Mouse L monolayers were incubated with or without antibody (10 μg/well) specific for the recombinant mouse interferon type I α/β receptor for 1 h at 37° C. This was removed and serum containing interferon (50% inhibitory endpoint of 1/120) added at 1/20 and 1/40 dilutions and incubated overnight to allow time for induction of the antiviral state. Medium was removed the next day and replaced with SFV. Incubation was continued at 37° C. Wells were examined daily under a light microscope for cytopathic effects (c.p.e.) caused by the virus, and scored at 3 days when the c.p.e. was maximal.

In addition, each plate contained a virus control, cell control and a positive interferon control—a commercially sourced recombinant mouse interferon-beta (PBL Biomedical Laboratories).

Table 19 (columns 2 and 4) show that serum interferon at both 1/20 and 1/40 dilutions completely inhibited the extensive cytopathic effect (c.p.e.) caused by SFV. However, when antibody to the recombinant mouse interferon type I α/β receptor was first added to cells (columns 3 and 5) maximum c.p.e. was evident indicating that the antibody had inhibited the interferon action, and thus that the virus inhibitory agent was indeed a type I interferon. Table 20 demonstrates the expected titration present on the same 96-well plate of our standard type I interferon-beta.

TABLE 19

Inhibition of mouse serum interferon activity by preincubation of the target mouse L cells with antibody to recombinant mouse interferon α/β receptor

| | Test for interferon activity | | | | Virus control | Cell control |
|---|---|---|---|---|---|---|
| Antibody to type I interferon receptor | − | + | − | + | − | − |
| Interferon (serum 1/20) | + | + | Na | Na | − | − |
| Interferon (serum 1/40) | Na | Na | + | + | − | − |

TABLE 19-continued

Inhibition of mouse serum interferon activity by preincubation of the target mouse L cells with antibody to recombinant mouse interferon α/β receptor

| | Test for interferon activity | | | | Virus control | Cell control |
|---|---|---|---|---|---|---|
| SFV | + | + | + | + | + | − |
| c.p.e. in L cells | − | ++++ | − | ++++ | ++++ | − |

Na, not applicable

++++ c.p.e. (cytopathic effect), destruction of ≥99% of the cell monolayer by SFV (Semliki Forest virus), − c.p.e., destruction of none of the cell monolayer;

c.p.e. was read daily and recorded at 3 days after infection.

TABLE 20

Titration of an interferon-beta standard from the same plate as Table 19

| | Number of interferon units/well ($log_{10}$) | | | | | | | | | | Virus control | Cell control |
|---|---|---|---|---|---|---|---|---|---|---|---|---|
| Interferon | 2.0 | 2.0 | 1.5 | 1.5 | 1.0 | 1.0 | 0.5 | 0.5 | 0 | 0 | None | None |
| c.p.e. | ++++ | ++++ | ++++ | ++++ | ++++ | + | − | − | − | − | ++++ | − |

++++ c.p.e., destruction of 99% of the cell monolayer,

− c.p.e., destruction of none of the cell monolayer

The SFV-inhibitory activity present in the serum of mice intraperitoneally injected with DI influenza A virus 244/PR8 was inhibited by antibody to the external domain of the interferon type I receptor, which therefore unequivocally identifies it as a type I interferon.

EXAMPLE 17

Demonstration that Type I Interferon is Induced in Cell Culture by DI Influenza A Viruses Non-infectious DI and UV-inactivated (iDI) viruses were used (see Table 22 below). All contained $2\times10^5$ haemagglutinating units (HAU)/ml. They were inoculated at the dilutions indicated (Table 22) on to a human lung cell line (A549) engineered to express a luciferase gene activated by an interferon promoter. The positive control for interferon induction was Newcastle disease virus (NDV) (see Table 21).

TABLE 21

Controls for induction of interferon in repeat assays

| | Experiment 1 | Experiment 2 |
|---|---|---|
| Negative control | 0.17* | 0.27 |
| Positive control (NDV) | 25.15 | 105.9 |

*luciferase levels;

NDV, Newcastle disease virus.

TABLE 22

Induction of interferon by DI influenza viruses

| | Dilu-tion | Experiment 1 | | | | Experiment 2 | |
|---|---|---|---|---|---|---|---|
| | | DI | DI* | iDI | iDI* | DI | iDI |
| 244/PR8 #793 | 1/1 | 10.87** | 45.76 | 0.26 | 1.1 | 5.27 | |
| | | 8.66 | 36.56 | 0.26 | 1.1 | 4.83 | |
| | 1/10 | 1.39 | 5.85 | 0.23 | 1.0 | Nd | |
| | | 1.76 | 7.41 | 0.23 | 1.0 | | |
| | 1/100 | 0.63 | 2.65 | Nd | Nd | Nd | |
| | | 0.51 | 2.15 | | | | |
| | 1/1000 | Nd | | | | 1.62 | |
| | | | | | | 1.34 | |
| 220/Vic #792 | 1/1 | | | | | 34.07 | 0.44 |
| | | | | | | 23.15 | 0.47 |
| | 1/10 | | | | | 14.37 | 0.49 |
| | | | | | | 8.86 | 0.4 |
| | 1/100 | | | | | 2.88 | Nd |
| | | | | | | 2.84 | |
| | 1/1000 | | | | | 0.65 | |
| | | | | | | 2.84 | |
| 220/PR8 #794 | 1/1 | | | | | 0.39 | 1.34 |
| | | | | | | 0.45 | 1.68 |
| | 1/10 | | | | | 0.45 | 0.23 |
| | | | | | | 0.48 | 0.32 |
| | 1/100 | | | | | 0.41 | Nd |
| | | | | | | 0.45 | |
| | 1/1000 | | | | | 0.4 | Nd |
| | | | | | | 0.41 | |

*luciferase valuesin column 4 and 6 have been normalized to the value of the positive NDV control in experiment 2 (105.9/25.25) (Table 1).

**luciferase levels.

Nd, not done

Table 22, experiment 1 shows that DI influenza A virus 244/PR8 induced interferon but inactivated DI influenza A virus did not (1.5× the negative control). Interferon induction titrated out, and interferon was induced by 1/10 DI influenza A virus. The value for 1/100 DI influenza A virus was probably not significant (although the negative control OD was 0.17, the 1/1000 value for DI influenza A virus 220/PR8 #794 was 0.4)

After normalizing according to the interferon induced by the NDV positive controls, the amount of interferon induced by DI influenza A virus 244/PR8 in experiment 1 was very similar to that stimulated by DI influenza A virus 220/Vic #792 in experiment 2, and both were higher than that made by DI influenza A virus 220/PR8 #794. Thus the ability to induce interferon is: 244/PR8=220/Vic>220/PR8.

DI influenza A virus 244/PR8 #793 induced about 2-fold less interferon (or 9-fold by the normalized value) in experiment 2—possibly the result of inactivation on storage or freeze-thawing.

The difference between the interferon stimulators (DI influenza A viruses 244/PR8, 220/Vic) and the non-stimulator (220/PR8) is striking, but is difficult to understand as 220/Vic and 220/PR8 have the same cloned DI 220 RNA. However, the high interferon levels of 244/PR8 #793 and 220/Vic #792 correlate well with the degree of protection of mouse from influenza B virus.

EXAMPLE 18

Demonstration that 24-Hour Pretreatment of Mice with DI Influenza A Virus Increases the Efficacy of Protection from Influenza B Virus Compared with Simultaneous Treatment Cloned DI influenza A virus 244/PR8 (1.2 and 0.12 μg/mouse) was given intranasally, as described above, to lightly anaesthetized mice either 24 hours before infection with influenza B/Lee/40 or simultaneously as a mixture with B/Lee. Non-specific effects of the DI virus were controlled by inactivating the DI virus by 8 minutes exposure to UV light. Mice were weighed daily and assessed for clinical disease. Data in Table 23, row 6 show that mice given active DI virus and B/Lee simultaneously all became sick and lost weight; although they were protected from more serious disease (as indicated by the greater weight loss) and death (row 7). By comparison, pretreatment with the same amount of active DI virus prevented all weight loss and nearly all clinical disease (row 2). Pretreatment with 10-fold more dilute active DI virus (0.1 μg, row 4) also provided some protection from clinical disease, its severity and prevented all deaths.

TABLE 23

Pretreatment of mice with DI influenza A virus increases the efficacy of protection from influenza B virus

| 1 | DI virus | Simultaneous challenge virus | Challenge virus after 24 hours | Clinical disease | Weight loss (%) | Death |
|---|---|---|---|---|---|---|
| 2 | 1.2 μg active | − | + | 1/5* | −3.7 | 0/5 |
| 3 | 1.2 μg inactivated | − | + | 5/5 | 10.6 | 3/5 |

TABLE 23-continued

Pretreatment of mice with DI influenza A virus increases the efficacy of protection from influenza B virus

| 1 | DI virus | Simultaneous challenge virus | Challenge virus after 24 hours | Clinical disease | Weight loss (%) | Death |
|---|---|---|---|---|---|---|
| 4 | 0.12 μg active | − | + | 4/5 | 5.8 | 0/5 |
| 5 | 0.12 μg inactivated | − | + | 5/5 | 19.4 | 4/5 |
| 6 | 1.2 μg active | + | − | 5/5 | 9.2 | 0/5 |
| 7 | 1.2 μg inactivated | + | − | 4/5 | 17.8 | 2/5 |
| 8 | 0 | − | + | 5/5 | 15.3 | 2/5 |

*1 mouse was sick for 1 day only.

Surviving mice in a similar experiment were given a high challenge dose of B/Lee at 3 weeks after infection, to test if those mice which had not suffered any overt clinical disease (cf Table 23, row 2) had developed a conventional immunity. All were completely protected suggesting that they had indeed been immunized by a silent infection with B/Lee (data not shown).

The invention claimed is:

1. A method of reducing or treating a viral infection in an individual human or animal comprising administering an interferon-inducing amount of a cloned defective interfering (DI) influenza A virus to the individual, wherein the viral infection is caused by a respiratory virus of Orthomyxoviridae or Paramyxoviridae, further wherein said respiratory virus is not influenza A.

2. The method of claim 1, wherein the DI virus is administered via mucosal administration.

3. The method of claim 1, wherein the viral infection is caused by human respiratory syncytial virus (HRSV).

4. The method of claim 1, wherein the viral infection is caused by an Influenza B virus.

5. The method of claim 1, wherein the Paramyxoviridae virus is a Pneumovirus or a Metapneumovirus.

6. The method of claim 5, wherein the Metapneumovirus is a human metapneumovirus (HMPRV).

* * * * *